(12) United States Patent
King et al.

(10) Patent No.: US 8,399,205 B2
(45) Date of Patent: Mar. 19, 2013

(54) DEVICE AND METHOD FOR SEPARATION, CONCENTRATION, AND/OR PURIFICATION OF CELLS

(75) Inventors: Michael R. King, Ithaca, NY (US); David G. Foster, W. Henrietta, NY (US); Woojin Han, Seoul (KR); Bryce A. Allio, Cochranton, PA (US)

(73) Assignee: The University of Rochester, Rochester, NY (US)

( * ) Notice: Subject to any disclaimer, the term of this patent is extended or adjusted under 35 U.S.C. 154(b) by 409 days.

(21) Appl. No.: 12/622,924

(22) Filed: Nov. 20, 2009

(65) Prior Publication Data

US 2010/0167372 A1 Jul. 1, 2010

Related U.S. Application Data

(63) Continuation-in-part of application No. 12/289,006, filed on Oct. 17, 2008, now Pat. No. 7,892,766, which is a continuation of application No. 11/335,573, filed on Jan. 20, 2006, now abandoned.

(60) Provisional application No. 61/116,459, filed on Nov. 20, 2008, provisional application No. 60/645,012, filed on Jan. 21, 2005, provisional application No. 60/682,843, filed on May 20, 2005, provisional application No. 60/696,797, filed on Jul. 7, 2005.

(51) Int. Cl.
*G01N 33/53* (2006.01)
(52) U.S. Cl. ........................................................ 435/7.2
(58) Field of Classification Search .................. None
See application file for complete search history.

(56) References Cited

U.S. PATENT DOCUMENTS

| | | | |
|---|---|---|---|
| 6,306,650 B1 | 10/2001 | Townes et al. | |
| 6,365,362 B1 | 4/2002 | Terstappen et al. | |
| 6,488,704 B1 | 12/2002 | Connelly et al. | |
| 6,607,921 B1* | 8/2003 | Hindsgaul et al. | 506/9 |
| 6,743,190 B2 | 6/2004 | Connelly et al. | |
| 6,793,642 B2 | 9/2004 | Connelly et al. | |
| 6,900,021 B1* | 5/2005 | Harrison et al. | 435/7.21 |
| 7,211,183 B2* | 5/2007 | Seul et al. | 204/549 |
| 7,326,563 B2* | 2/2008 | Kim et al. | 435/288.5 |
| 7,892,766 B2* | 2/2011 | King et al. | 435/7.2 |
| 2002/0027431 A1 | 3/2002 | Tsuruki | |
| 2003/0007897 A1* | 1/2003 | Creasey | 422/100 |
| 2003/0113478 A1 | 6/2003 | Dang et al. | |
| 2004/0191246 A1* | 9/2004 | Connelly et al. | 424/140.1 |
| 2006/0127925 A1* | 6/2006 | Stayton et al. | 435/6 |
| 2006/0234210 A1 | 10/2006 | Kenan et al. | |
| 2007/0178084 A1* | 8/2007 | King et al. | 424/140.1 |
| 2009/0022768 A1* | 1/2009 | King et al. | 424/422 |
| 2010/0112026 A1* | 5/2010 | Karp et al. | 424/422 |
| 2010/0304485 A1* | 12/2010 | Karnik et al. | 435/375 |

FOREIGN PATENT DOCUMENTS

WO 2006078994 A2 7/2006

OTHER PUBLICATIONS

Cummings; Structure and function of the selectin ligand PSGL-1; Brazilian Journal of Medical and Biological Research, 1999, vol. 32; pp. 519-528.

Lasky et al.; An Endothelial Ligand for L-Selectin Is a Novel Mucin-like Molecule; Cell, Jun. 12, 1992, vol. 69; pp. 927-938.

Aigner et al.; CD24, a Mucin-Type Glycoprotein, Is a Ligand for P-Selectin on Human Tumor Cells; Blood, May 1, 1997, vol. 89, No. 9; pp. 3385-3395.

\* cited by examiner

*Primary Examiner* — Ann Lam
(74) *Attorney, Agent, or Firm* — Hodgson Russ LLP

(57) ABSTRACT

The present invention relates to methods and apparatuses for cell separation. In particular, the invention relates to separation of a particular cell type from a mixture of different cell types based on the differential rolling property of the particular cell type on a substrate coated with molecules that exhibits adhesive property with the particular cell type. The molecules can be directly coated on the surface or coated on nanoparticles that are adhered to the surface. This technology is adaptable for use in implantable shunts and devices for cell trafficking or tumor neutralization.

9 Claims, 23 Drawing Sheets

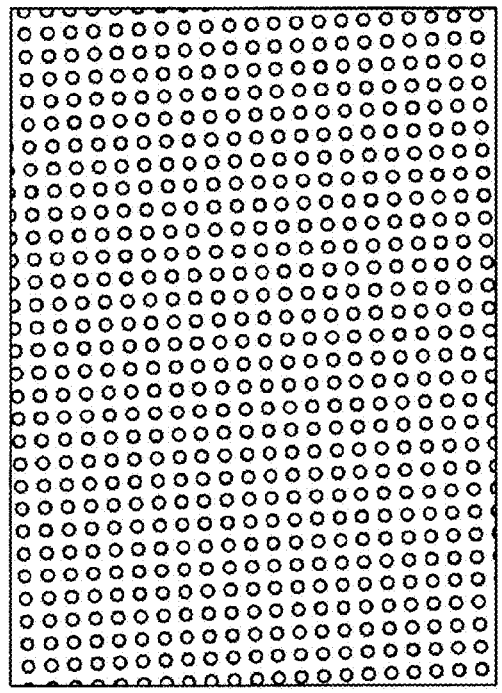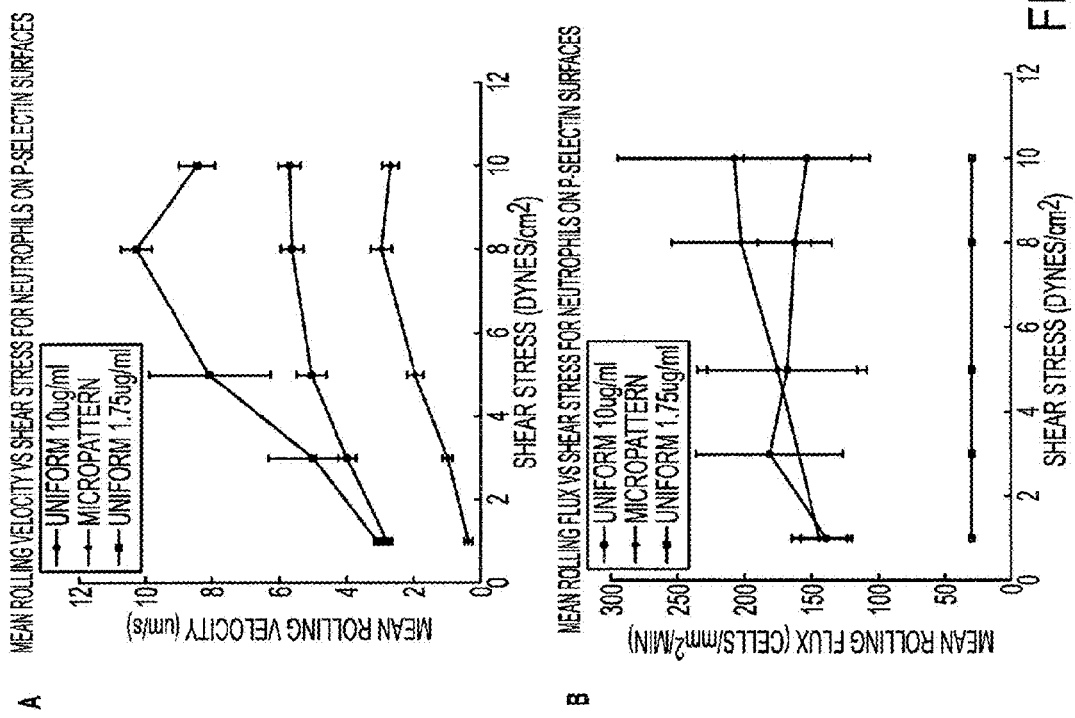
FIG. 4

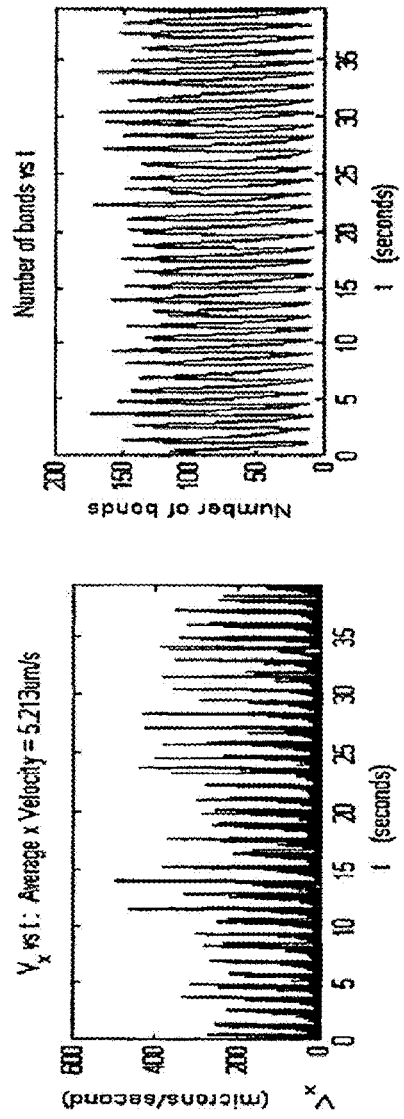
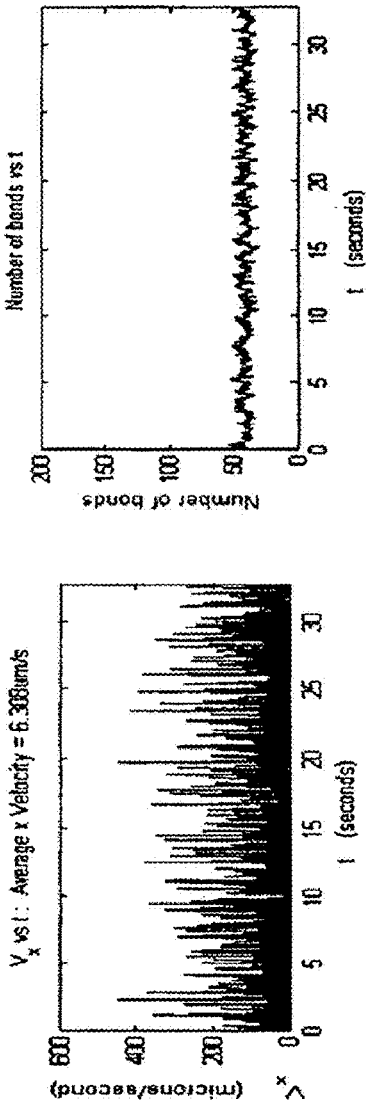
FIGURE 5

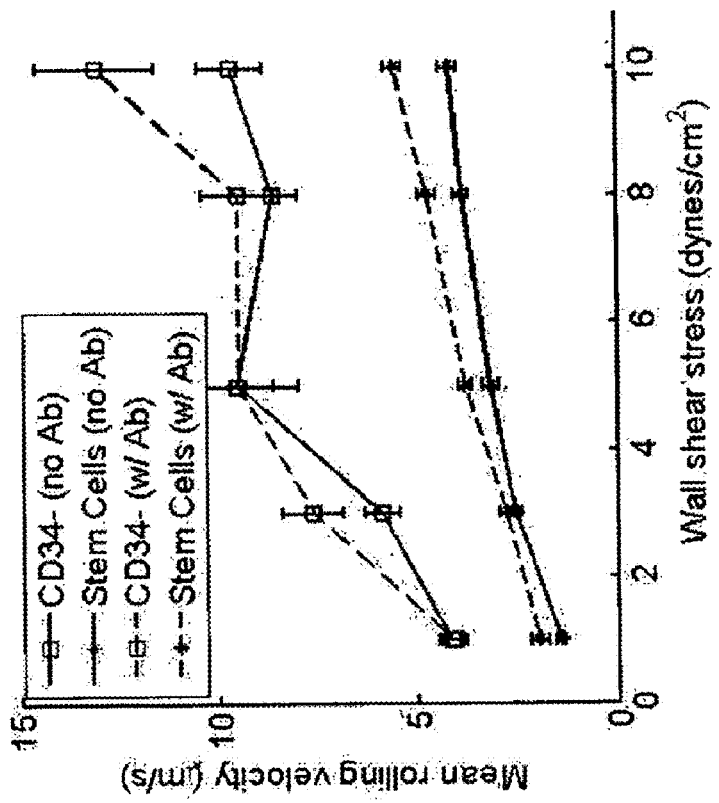
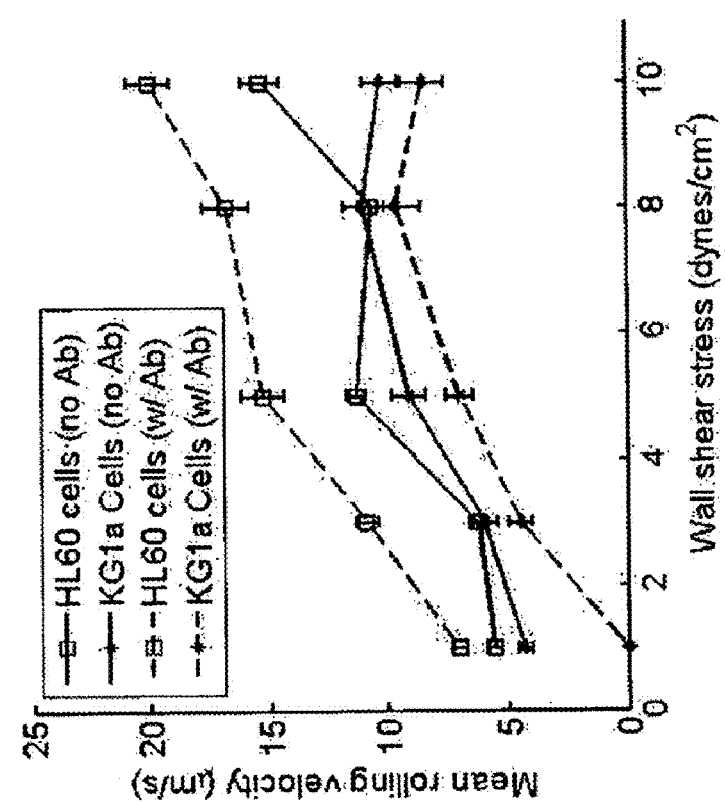
FIGURE 6

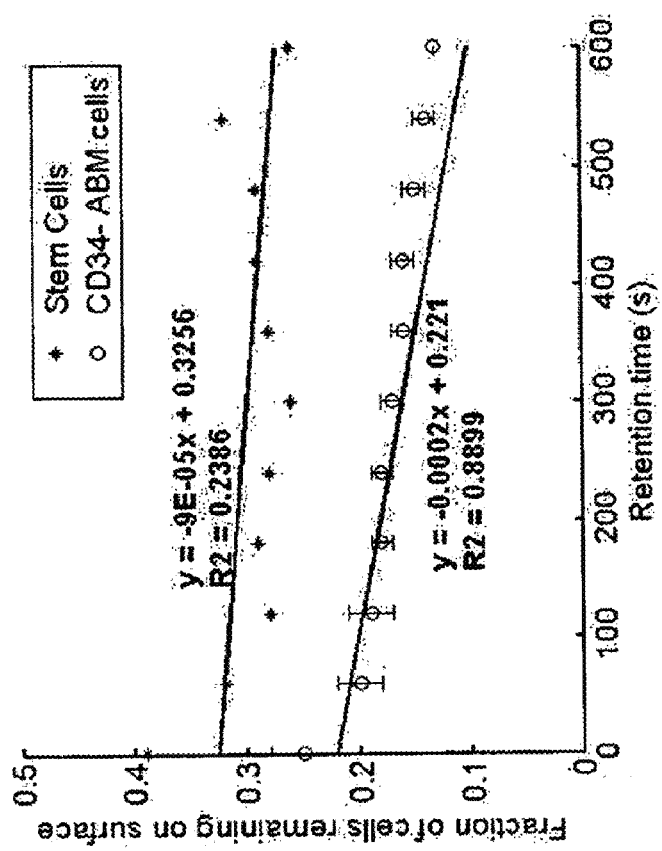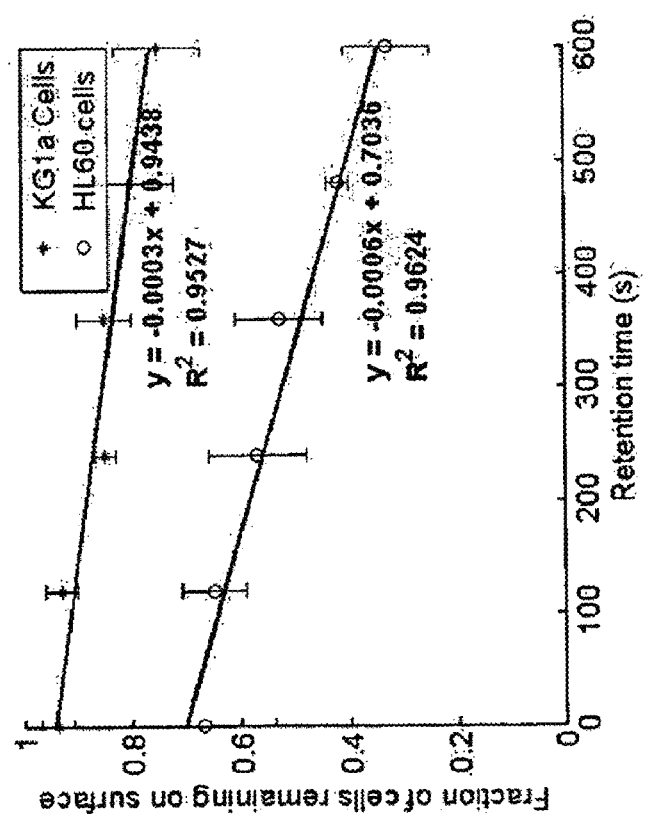
FIGURE 7

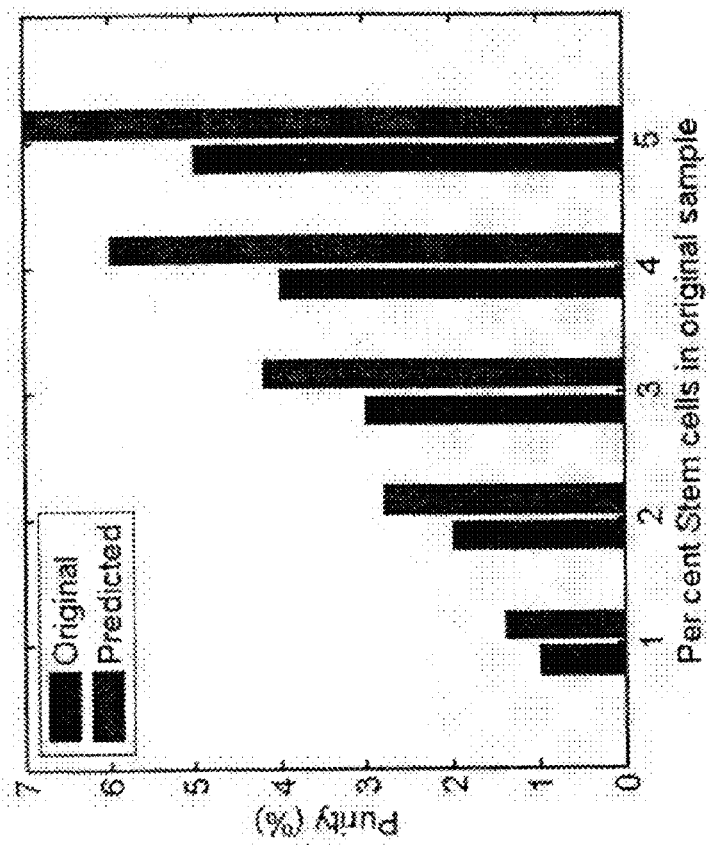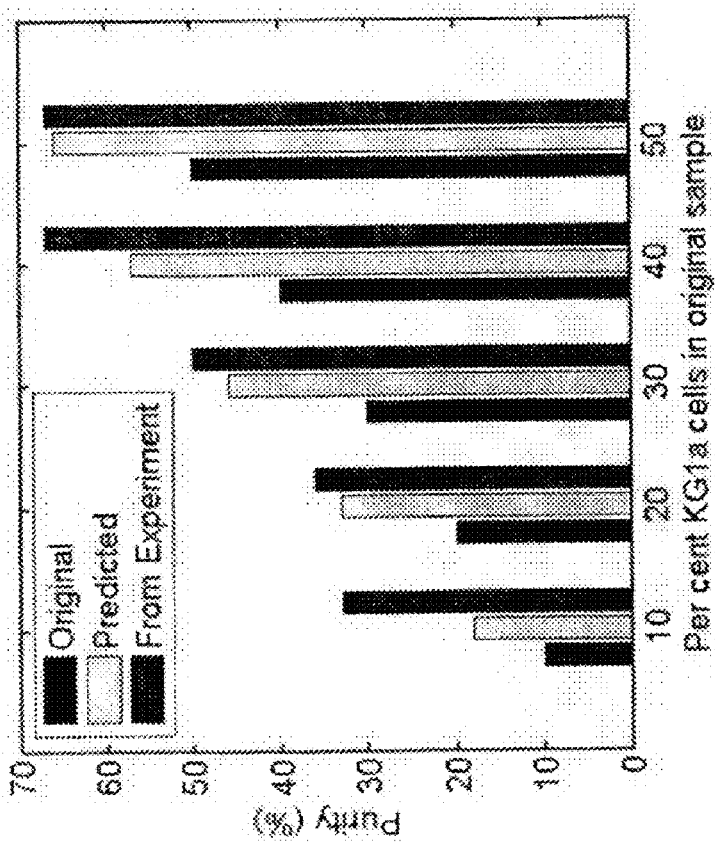
FIGURE 8

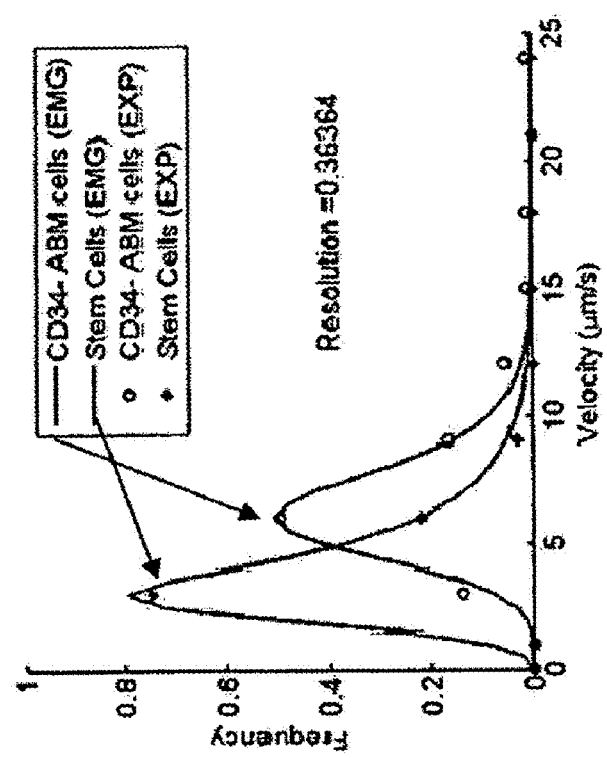
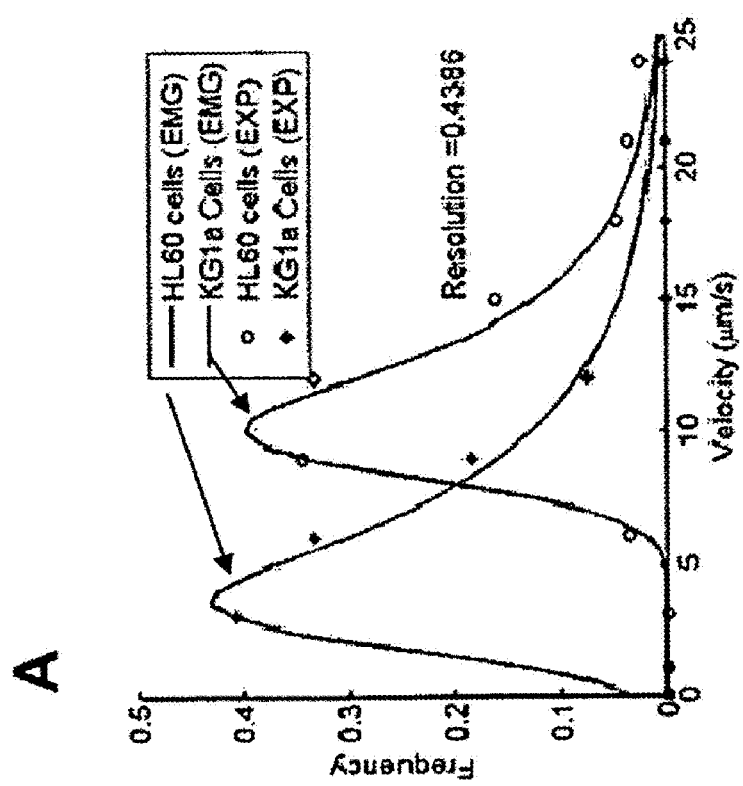
FIGURE 11

DEVICE AND METHOD FOR SEPARATION, CONCENTRATION, AND/OR PURIFICATION OF CELLS

CROSS-REFERENCE TO RELATED APPLICATIONS

This application claims priority to U.S. Provisional application No. 61/116,459, filed on Nov. 20, 2008, and is also a continuation-in-part of U.S. application Ser. No. 12/289,006, filed on Oct. 17, 2008 now U.S. Pat. No. 7,892,766, which is a continuation of U.S. application Ser. No. 11/335,573 filed Jan. 20, 2006 now abandoned and claims priority of U.S. Provisional Patent Application Nos. 60/696,797, filed Jul. 7, 2005; 60/682,843, filed May 20, 2005; and 60/645,012, filed Jan. 21, 2005; which are incorporated herein by reference.

FIELD OF THE INVENTION

The present invention relates to methods and apparatuses for cell separation. In particular, the invention relates to separation of a particular cell type from a mixture of different cell types based on the differential rolling property of the particular cell type on a substrate coated with molecules that exhibits adhesive property with the particular cell type.

BACKGROUND OF THE INVENTION

Purified cell populations have many applications in biomedical research and clinical therapies (Auditore-Hargreaves et al., Bioconjug. Chem. 5:287-300, 1994; and Weissman, Science 287:1442-1446, 2000). Often, cells can be separated from each other through differences in size, density, or charge. However, for cells of similar physical properties, separation is often accomplished by exploiting differences in the presentation of molecules on the cell surface. Cell-affinity chromatography is based on this approach, most often by employing immobilized antibodies to specific cell surface antigens. Such affinity column separations require several distinct steps including incubation of the cells with the antibody, elution of the cells, cell collection, and release of the conjugated antibody, with each step reducing the overall yield of cells and increasing the cost of the process.

There exists a need for obtaining cellular samples from donors that are enriched in desired biological targets. Because a heterogeneous sample may contain a negligible amount of a biological entity of interest, the limits of separation methods to provide viable and potent biological target in sufficient purity and amount for research, diagnostic or therapeutic use are often exceeded. Because of the low yield after separation and purification, some cell-types, such as stem cells, progenitor cells, and immune cells (particularly T-cells) must be placed in long-term culture systems under conditions that enable cell viability and clinical potency to be maintained and under which cells can propagate (cell expansion). Such conditions are not always known to exist. In order to obtain a sufficient amount of a biological target, a large amount of sample, such as peripheral blood, must be obtained from a donor at one time, or samples must be withdrawn multiple times from a donor and then subjected to one or more lengthy, expensive, and often low-yield separation procedures to obtain a useful preparation of the biological target. Taken together, these problems place significant burdens on donors, separation methods, technicians, clinicians, and patients. These burdens significantly add to the time and costs required to isolate the desired cells.

Stem cells are capable of both indefinite proliferation and differentiation into specialized cells that serve as a continuous source for new cells that comprise such tissues as blood, myocardium and liver. Hematopoietic stem cells are rare, pluripotent cells, having the capacity to give rise to all lineages of blood cells (Kerr, Hematol./Oncol. Clin. N. Am. 12:503-519, 1998). Stem cells undergo a transformation into progenitor cells, which are the precursors of several different blood cell types, including erythroblasts, myeloblasts, monocytes, and macrophages. Stem cells have a wide range of potential applications, particularly in the autologous treatment of cancer patients.

Typically, stem cell products (true stem cells, progenitor cells, and CD34+ cells) are harvested from the bone marrow of a donor in a procedure, which may be painful, and requires hospitalization and general anesthesia (Recktenwald et al., Cell Separation Methods and Applications, Marcel Dekker, New York, 1998). More recently, methods have been developed enabling stem cells and committed progenitor cells to be obtained from donated peripheral blood or peripheral blood collected during a surgical procedure.

Progenitor cells, whether derived from bone marrow or peripheral blood, can be used to enhance the healing of damaged tissues (such as myocardium damaged by myocardial infarction) as well as to enhance hematologic recovery following an immunosuppressive procedure (such as chemotherapy). Thus, improved approaches to purify stem cells ex vivo, or to "re-address" circulating stem cells in vivo, has great potential to benefit the public health.

Hematopoietic stem and precursor cells (HSPC) are able to restore the host immune response through bone marrow transplantation, yet the demand for these cells far exceeds the available supply. HSPC also show great promise for treatment of other hematological disorders. HSPC are believed to adhesively roll on selectins during homing to the bone marrow in a manner analogous to the (much better understood) process of leukocyte trafficking Previous work has demonstrated that CD34+ cells (showing a marker of stem cell immaturity) roll more slowly and in greater numbers than more differentiated CD34− cells. By exploiting this difference in rolling affinity it is possible to construct a flow chamber device for continuous separation and purification of CD34+ cells from an initial mixture of blood cells, while maintaining viability of the cells for subsequent use in clinical applications. Such a process holds several distinct advantages over current affinity column methods. The feasibility of cell separation based on rolling affinity has been demonstrated by others for artificial adhesive microbeads, and by us for live stem cell populations.

CD34 is a surface marker of stem cell immaturity. Recent work has shown that CD34+ cells from the adult bone marrow and fetal liver roll more slowly and to a greater extent on P- and L-selectin, compared to CD34− cells (Greenberg et al., Biophys. J. 79:2391-2403, 2000). Further, Greenberg et al. (Biotechnol. Bioeng. 73:111-124, 2001) demonstrated that rolling affinity-based separations of carbohydrate-coated microspheres is possible. However, there remains a need for methods and apparatus for separation of a particular type of cells, particularly, immature stem cells from other cells, such as more mature cells, in a continuous, single-pass, high-throughput flow chamber.

SUMMARY OF THE INVENTION

Applicants have discovered a novel method and apparatus for continuous separation or purification of cells by taking advantage of differential rolling velocities of different cell types. Generally, cells roll at about the same velocity on a surface; however, applicant have discovered that if a surface is rendered "sticky" to a particular cell type while not affecting other cells, the particular cell type exhibits a different rolling velocity and the other cells. By taking advantage of the difference in rolling velocity, the particular cell type can be separated, concentrated, or purified from a cell mixture.

The advantage of the present invention is that it requires fewer steps and subjects the cells to a more physiologically relevant environment, as opposed to the artificial and harsh environment utilized by current other methods of cell separation. The present invention does not use expensive purified antibodies, and is cheaper, faster, and more efficient. The present device will enable physicians to treat cancers, immunodeficiency, hematological, and, potentially, cardiac diseases with greater efficacy.

The device of the present invention contains a surface for cell rolling, wherein the surface has been coated with a substance that chemically or physically adheres to the type of cell being separated, concentrated, or purified (the desired cells). In use, a mixture of cells is allowed to flow along the surface. Because the desired cells roll at a different velocity than the other cells in the mixture due to the adhesion between the desired cells and the coated surface, it can be separated, concentrated, or purified from the other cells.

The adhesion molecule may be specific for a region of a protein, such as a prion, a capsid protein of a virus or some other viral protein, and so on. A target specific adhesion molecule may be a protein, peptide, antibody, antibody fragment, a fusion protein, synthetic molecule, an organic molecule (e.g., a small molecule), or the like. In general, an adhesion molecule and its biological target refer to a ligand/anti-ligand pair. Accordingly, these molecules should be viewed as a complementary/anti-complementary set of molecules that demonstrate specific binding, generally of relatively high affinity. Cell surface moiety-ligand pairs include, but are not limited to, T-cell antigen receptor (TCR) and anti-CD3 mono or polyclonal antibody, TCR and major histocompatibility complex (MHC)+antigen, TCR and super antigens (for example, staphylococcal enterotoxin B (SEB), toxic shock syndrome toxin (TSST), etc.), B-cell antigen receptor (BCR) and anti-immunoglobulin, BCR and LPS, BCR and specific antigens (univalent or polyvalent), NK receptor and anti-NK receptor antibodies, FAS (CD95) receptor and FAS ligand, FAS receptor and anti-FAS antibodies, CD54 and anti-CD54 antibodies, CD2 and anti-CD2 antibodies, CD2 and LFA-3 (lymphocyte function related antigen-3), cytokine receptors and their respective cytokines, cytokine receptors and anti-cytokine receptor antibodies, TNF-R (tumor necrosis factor-receptor) family members and antibodies directed against them, TNF-R family members and their respective ligands, adhesion/homing receptors and their ligands, adhesion/homing receptors and antibodies against them, oocyte or fertilized oocyte receptors and their ligands, oocyte or fertilized oocyte receptors and antibodies against them, receptors on the endometrial lining of uterus and their ligands, hormone receptors and their respective hormone, hormone receptors and antibodies directed against them, and others. Other examples may be found by referring to U.S. Pat. No. 6,265,229; U.S. Pat. No. 6,306,575 and WO 9937751, which are incorporated herein by reference. Most preferably, the adhesion molecules are antibodies, selectins, cadherins, integrins, mucin-like family, immunoglobin superfamily or fragments thereof. The adhesion between the selected cells and the adhesion molecule is preferably transient, such that when exposed to the shear rate of a flow field, preferably in the range of 50-1000 $s^{-1}$ (0.5 to 10 dynes/$cm^2$ and all integers and values to the tenth decimal place therebetween) and all integers therebetween, the cells do not bind too tightly to the adhesion molecule, but rather roll along the coated surface.

Adhesion molecules can be coated on the surface by directly physisorbing (absorbing) the molecules on the surface. Alternatively, the adhesion molecules can be covalently attached to the surface by reacting—COOH with—$NH_2$ groups on silanated glass surfaces. Another method for attachment of adhesion molecules is to first absorb or attach avidin protein (including variants such as "Neutravidin" or "Superavidin") to the surface, and then reacting this avidin-coated surface with adhesion molecules containing a biotin group. Electrostatic charge or hydrophobic interactions can be used to attach adhesion molecules on the surface. Other methods of attaching molecules to surfaces are apparent to those skilled in the art, and depend on the type of surface and adhesive molecule involved.

The adhesion molecules can be directly attached to the surface or can be attached to nanoparticles which are immobilized on the surface. By "immobilized" is meant that the nanoparticles will remain attached to the inner surface at shear stress generated by flow of fluid through such as under physiological shear stress (generally between 0.5 to 10 dynes/$cm^2$). For example, in one embodiment, the nanoparticles are silica nanoparticles which have adhesion molecules attached thereto. The nanoparticles can be immobilized on to the surface via the use of organic or inorganic adhesive layers (such as poly-L-lysine or metal oxides). In one embodiment, the nanoparticles can be between 10-200 nm (and all integers therebetween) and can be of any biocompatible material which can attach to the inner surface of a microtube/device of at the present invention (such as gold nanoparticices).

In a preferred embodiment, the adhesive molecule is micropatterned on the rolling surface to improve separation, concentration, and/or purification efficiency. The pattern is preferably a punctate distribution of the adhesive molecule as described by King (Fractals, 12(2):235-241, 2004), which is incorporated herein by reference. Here, punctate refers to adhesion molecule concentrated in small discrete spots instead of as a uniform coating, which can be in any variety of patterns Punctate micropatterns or other micropatterns can be produced through microcontact printing. This is where a microscale stamp is first incubated upside-down with the adhesion molecule solution as a drop resting on the micropatterned (face-up) surface. Then the drop is aspirated off, the microstamp surface quickly blown dry with nitrogen gas, and then the microstamp surface quickly placed face down on the substrate. A small 10-20 g/cm.sup.2 weight can be added to the stamp to facilitate transfer of the adhesion molecule onto the substrate. Then the substrate is removed and a micropattern of adhesion molecule remains on the surface.

FIG. 4 compares the adhesion of flowing cells on either micropatterned or uniform adhesive surfaces. In FIG. 4A, the average rolling velocity of cells on a micropattern is significantly lower than on a uniform surface of equal average density, and the micropattern is even slower than a uniform surface with a much higher average density. In FIG. 4B, it is shown the rolling flux (number of adhesively rolling cells) is high on the micropattern, is high on the uniform surface with a much higher average density than the micropattern, and is low on the uniform surface with average density matched to the micropattern. Thus, micropatterns of adhesive molecule can be used to capture specific flowing cells much more effectively and efficiently than uniform adhesive surfaces. FIG. 4C shows a picture of a punctate micropattern of adhesive molecule, 3.times.3 micron squares of P-selectin micropatterned on tissue culture polystyrene.

FIG. 5 shows the rolling velocity and the number of molecular adhesion bonds from a computer simulation of adhesion of a flowing cell to an adhesive surface with a (A) micropattern of molecule or (B) a uniform coating of adhesive molecule. FIG. 5 shows that over the micropattern ("punctate") distribution that the velocity and number of bonds fluctuates in a oscillatory, periodic way, whereas on the uniform surface the fluctuations are random. Thus, micropatterned molecular surfaces can be used to deliver regular, periodic surface signals to flowing cells.

FIG. 13 shows a different micropattern of adhesion molecule consisting of repeating linear stripes. Cells flowing past the micro-striped surface adhere to the surface and roll along. If the stripes are aligned at an angle to the direction of flow, then the cells follow the stripe and can be moved perpendicular to the flow direction. Thus, stripes of adhesion molecules can be used to "steer" rolling cells in one direction or the other, and the cells can be led into various chambers at the end of the flow device and sorted in this way. One embodiment is to use microstripes of adhesion molecules to "steer" targeted adhesive cells into a side chamber for storage and later retrieval, while allowing most cells or weakly adherent cells to pass through the device and not be "steered" towards the holding chamber.

In a particularly preferred embodiment, the invention exploits the natural rolling properties of hematopoetic stem cells (HSCs), separating them from other blood cells in a method that is simpler, faster, cheaper, and more effective than current solutions. A novel feature is using the differential rolling properties to separate out HSCs from other cells in the blood. In this embodiment, the blood cells are rolled along a surface coated with selectin proteins. The adhesion between the selectins and the HSC retards the rolling rate of HSC along the surface, while other cells rolls their normal rate. The difference in rolling rates concentrates and separates the HSCs from the other cells.

A particularly useful application of the present invention is the separation of HSCs for use in the treatment of many cancers, hematological, and immunodeficiency diseases. The treatment of cancers and immune diseases require aggressive radiation and chemotherapy that kills healthy bone marrow required for blood production. Bone marrow and peripheral HSC transplantation enables doctors to replace the diseased or destroyed bone marrow with health marrow that produces normal blood cells. The problem our device solves is how to separate HSC's out of the peripheral blood supply for later readmission to the body. Our approach to the solution is to separate HSCs in flow chambers. The flow chamber surfaces are coated with selectin proteins that slow down and separate HSCs from the rest of the blood cells.

In an embodiment of the present invention, an implantable device is provided to effect in vivo cell separation, concentration, and/or purification in bodily fluid. The implantable device preferably contains a chamber having a surface, through which the bodily fluid passes, that is coated with an adhesion molecule that selectively adheres to a desired cell type. The implantable device refers to any article that may be used within the context of the methods of the invention for changing the concentration of a cell of interest in vivo. An implantable device may be, inter alia, a stent, catheter, cannula, capsule, patch, wire, infusion sleeve, fiber, shunt, graft, and so on. An implantable device and each component part thereof may be of any bio-compatible material composition, geometric form or construction as long as it is capable of being used according to the methods of the invention. The literature is replete with publications that teach materials and methods for constructing implantable devices and methods for implanting such devices, including: U.S. Pat. Nos. 5,324,518; 5,976,780; 5,980,889; 6,165,225; U.S. Patent Publication 2001/0000802; U.S. Patent Publication 2001/0001817; U.S. Patent Publication 2001/0010022; U.S. Patent Publication 2001/0044655; U.S. Patent Publication 2001/0051834; U.S. Patent Publication 2002/0022860; U.S. Patent Publication 2002/0032414; U.S. Patent Publication 2004/0191246; EP 0809523; EP 1174156; EP 1101457; and WO 9504521, which are incorporated herein by reference.

In an embodiment, the implantable device of the present invention contains chamber whose surfaces are coated with adhesive molecules, such as selectin, integrins, cadherins, mucins, immunoglobin superfamily, and cadherins, and a molecule that neutralizes the tumor-forming capacity of the circulating cancer cells, such as TRAIL (signal TNF-related apoptosis-inducing ligand), Fas ligand, and chemotherapeutic drug, (e.g. doxorubicin). The tumor neutralizing molecule can connected to the surface by a molecular stalk that can be cleaved by the cell surface metalloproteases and then enter the cell. This cleavable form is useful for drugs that need to be internalized by cells, rather than surface ligands such as TRAIL. In this embodiment, the implantable device retards the rolling of cancer cells along its wall, while TRAIL kills the cancer cells slowly rolling along the coated surface of the device before they are released from the flow chamber back into the circulation. The device, once implanted in a patient, screens circulating blood and neutralize the tumor forming potential of circulating metastatic cancer cells without interruption of blood flow. This technology has the potential to provide significant benefit as an adjunct cancer therapeutic to prevent the spread of metastatic tumors, which have a significant impact on cancer related mortality and degradation of quality of life. Furthermore, this technology has the potential to be tuned for specific cancers to increase its effectiveness by customizing the geometric constraints, molecular interactions, and applied therapeutic agents to optimize potency against specific cancer types.

BRIEF DESCRIPTION OF THE DRAWINGS

FIG. 4 is a diagram of experimental results demonstrating the assertion of the inventors that P-Selectin can be used to selectively slow cells as they encounter a surface coated with said protein. (A) Mean rolling velocity v. shear stress; (B) mean rolling flux v. shear stress; and (C) a punctated pattern of adhesion molecules on a surface.

FIG. 5 is a diagram describing the interaction of cells with a coated surface.

FIG. 6 shows cell rolling velocity as a function of wall shear rate. (A) KG1a (blue lines) and HL60 (red lines) cells roll at similar velocities on 0.5.mu.g/ml P-selectin only but in the presence of 40.mu.g/ml anti-CD34 (dashed lines), KG1a cells roll significantly slower than HL60 cells. (B) CD34+ HSPCs (blue lines) roll significantly slower than CD34− ABM cells (red lines) on 0.5.mu.g/ml P-selectin.+− 0.40.mu.g/ml anti-CD34.

FIG. 7 shows surface cell retention of CD34+ and CD34− cells. (A) KG1a cells (black line) had higher retentions than HL60 cells (blue line) on 0.5.mu.g/ml P-selectin and 40.mu.g/ml anti-CD34. (B) Similarly, CD34+ HSPCs (black line) had higher retentions than CD34− ABM cells (blue line) on 0.5.mu.g/ml P-selectin only. These experiments were performed at 3 dyn/cm.sup.2 for 10 minutes.

FIG. 8 shows experimental confirmation of computer simulation (A) We predict (green bars) and confirm with experiments (red bars) that there should be significant enrichment of KG1a cells on the P-selectin/antibody surface. The original concentrations (blue bars) are included for easier observations. (B) A more modest increase in CD34+ HSPCs purity (red bars) should be possible with our current system.

FIG. 11 shows velocity distribution of cells at 3 dyn/cm.sup.2. Experimental data fitted to exponentially modified Gaussian for (A) HL60/KG1a cells, (B) HSPC/CD34− ABM cells, all at 3 dyn/cm.sup.2.

DETAILED DESCRIPTION OF THE PREFERRED EMBODIMENTS

Because perfusion flow rates and selectin density on the chamber wall can both be used to control the average rolling velocity, computer simulations (using a computer algorithm called multiparticle adhesive dynamics (MAD) designed by the inventor specifically to study the adhesion of complex suspensions of cells to surfaces under flow) are used to determine the optimal conditions that cause CD34+ cells to downregulate their L-selectin expression while they are in close contact with the surface.

Figure 1:
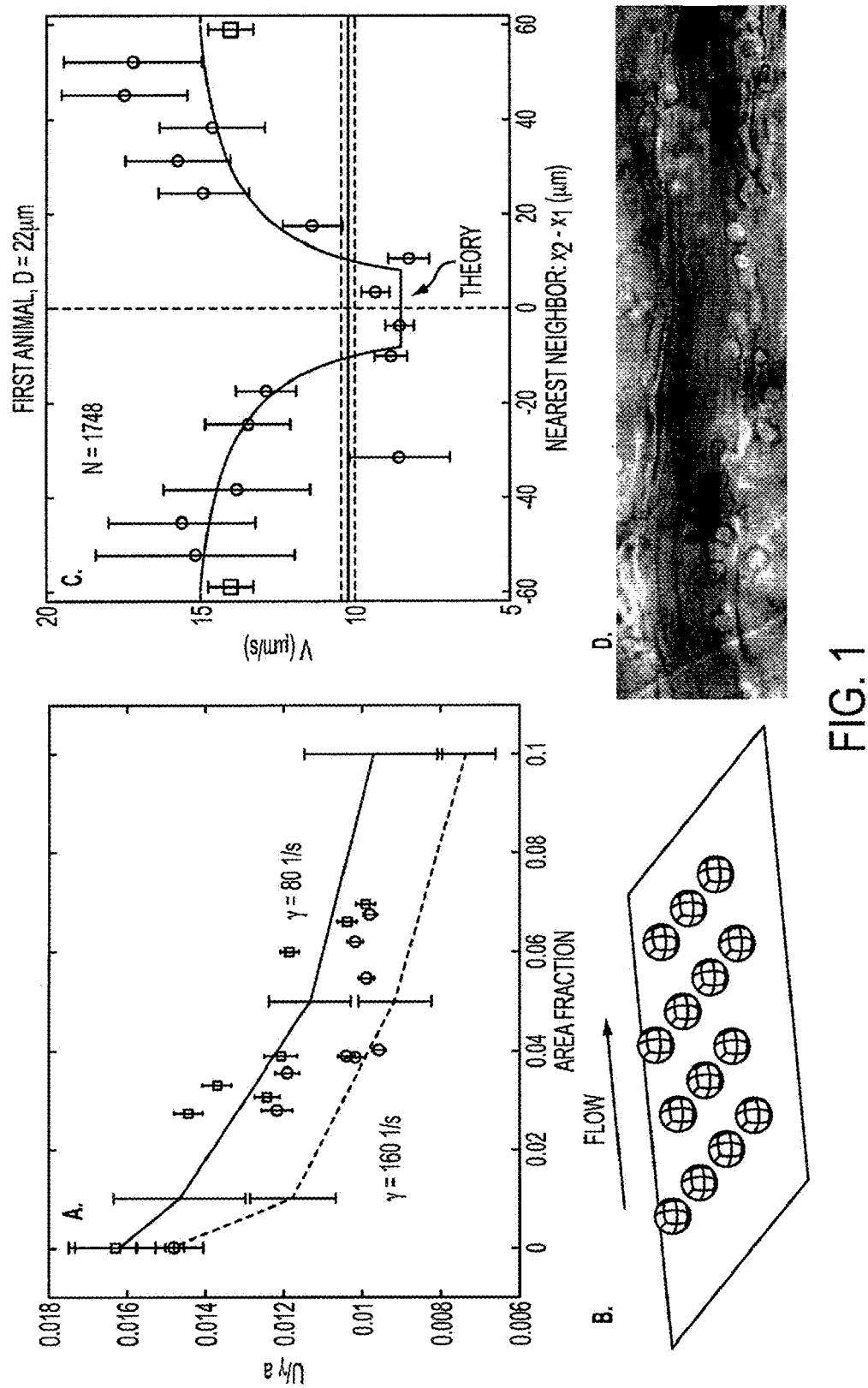
FIG. 1 describes experiments using the MAD computer simulation program: (A) Dimensionless rolling velocity of a collection of nearby cells as a function of the area fraction of adherent cells on the surface, obtained from either computer simulations (solid and dashed lines) or in vitro experiments (symbols) with sLex-coated beads rolling on P-selectin. (B) Diagram of the hexagonal array of 14 spheres used in MAD simulations of A. (C) Measured rolling velocity of leukocytes in a live mouse microvessel as a function of the center-to-center distance between each cell and the nearest neighboring cell. Data is compared to a simple 1/r hydrodynamic scaling argument. (D) Captured image of a typical post-capillary venule in mouse cremaster muscle under mildly inflammatory conditions.

Using the MAD computer algorithm, simulations have previously shown that the adhesive dynamics simulation can accurately predict the rolling velocity and rolling fraction of cells as a function of shear rate, selectin density and species, and PSGL-1 density on the leukocyte (King et al., Biophys. J. 81:799-813, 2001; and King et al., Proc. Natl. Acad. Sci. USA. 98:14919-14924, 2001). Thus, the computer simulation can be used to generate design parameters that optimize the performance of the separation device. A key parameter that the simulations will determine is the optimal delay time until the perfusion buffer is switched from calcium-containing to calcium-free media, in order to release the slowly rolling CD34+ cells from the surface into the final outlet fractions (See FIG. 1).

The applicant developed this entirely new algorithm to study multiparticle cell adhesion under flow, that builds on early work in AD. AD is a computational algorithm designed to simulate the adhesion of a rigid spherical cell to a planar surface in linear shear flow (Hammer et al., Biophys. J. 62:35-

57, 1992; Chang et al., Proc. Natl. Acad. Sci. USA. 97:11262-11267, 2000). The AD algorithm tracks the motion of each molecular bond between the cell and substrate as the cell rolls over or moves relative to the other surface. Bonds are stochastically formed and broken according the instantaneous probability of formation and failure as dictated by the instantaneous length (or hypothetical length in the case of an unformed bond) of a compliant spring with endpoints on either surface. Other surface interactions such as electrostatic repulsion, and body forces such as gravity, are included in the model.

To address these and other limitations of the original AD algorithm, MAD was developed. This approach is based on a boundary elements method for calculation of the hydrodynamic mobilities of a suspension of small particles in a viscous fluid (Kim et al., Microhydrodynamics: Principles and Selected Applications, Butterworth-Heinemann, Stoneham, Mass., 1991). This method, called CDL-BIEM is of general applicability, in that it can consider any number of arbitrarily-shaped particles in a general flow field confined by an arbitrary set of bounding surfaces. A modification of CDL-BIEM exists to consider elastically-deformable particles (Phan-Thien et al., ZAMP 47:672-694, 1996), and the method is computationally efficient insofar as being an 0(N.sup.2) process (where N is the number of boundary elements) and is easily parallelizable (Fuentes et al., AIChE J. 38:1059-1078, 1992; and Amann et al., Eng. Anal. Bound. Elem. 11:269-276, 1993). This multiparticle hydrodynamic calculation was fused to an improved version of AD.

Figure 2:
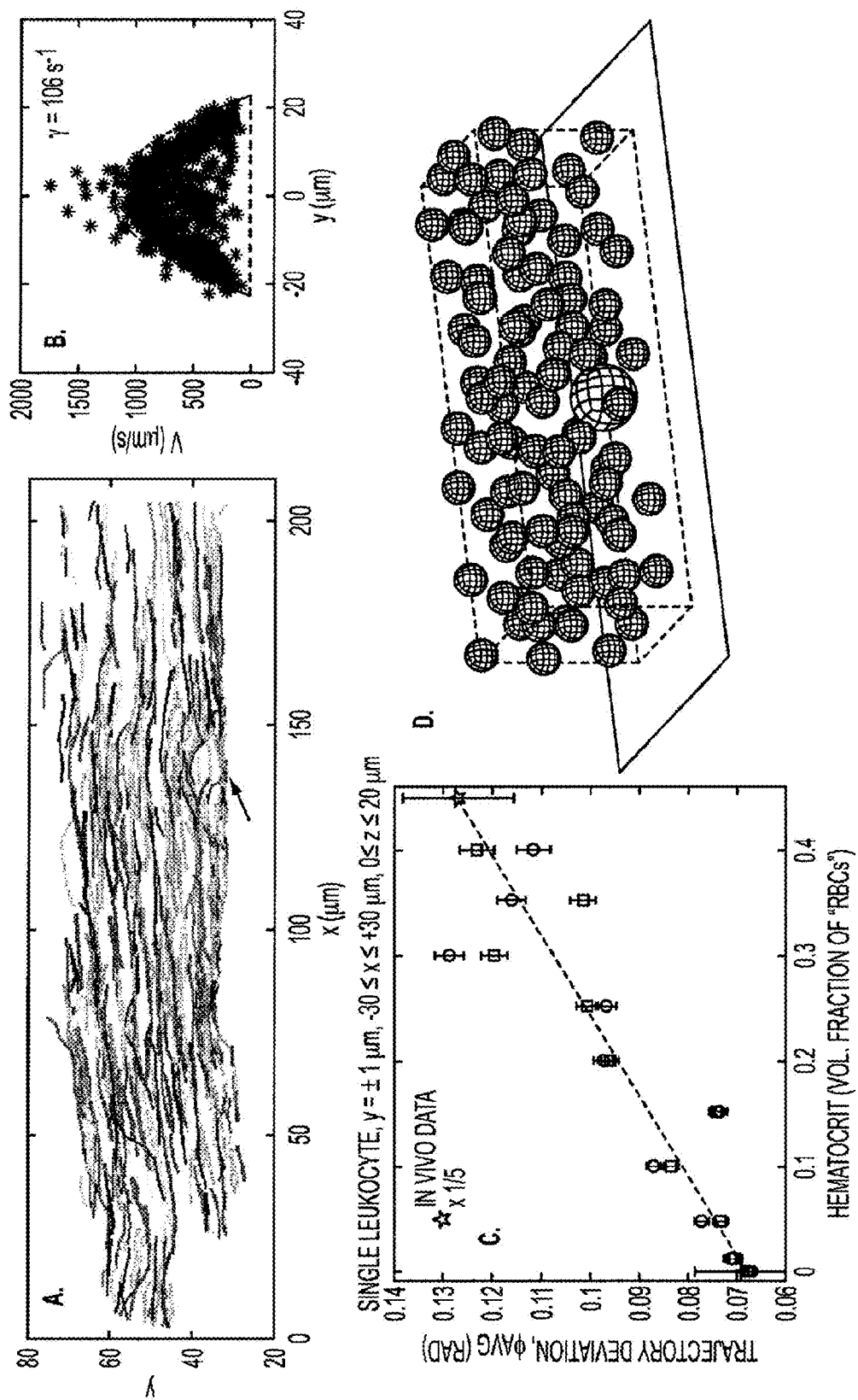
FIG. 2 describes experiments using the MAD computer simulation program: (A) Representative trajectories of fluorescent tracer beads in a 40.mu.m venule in mouse cremaster muscle. The arrow denotes the position of a leukocyte adherent on the vessel wall. (B) The velocity profile in the microcirculation is approximately parabolic. (C) A random distribution of red blood cells increases the average deflection angle of the flow. The trajectory deviation angle from horizontal was found to increase monotonically with increasing hematocrit in the numerical simulation (squares, circles), and in the in vivo experiments (stars). Note that the in vivo data have been reduced by a factor of 5 to account for the fact that real vessels are not mathematically smooth surfaces, and have some inherent non-uniformity. (D) In the computational model the red blood cells were modeled as rigid spheres with volume equal to that of a mature red blood cell. The case shown corresponds to 40% hematocrit.
Figure 3:
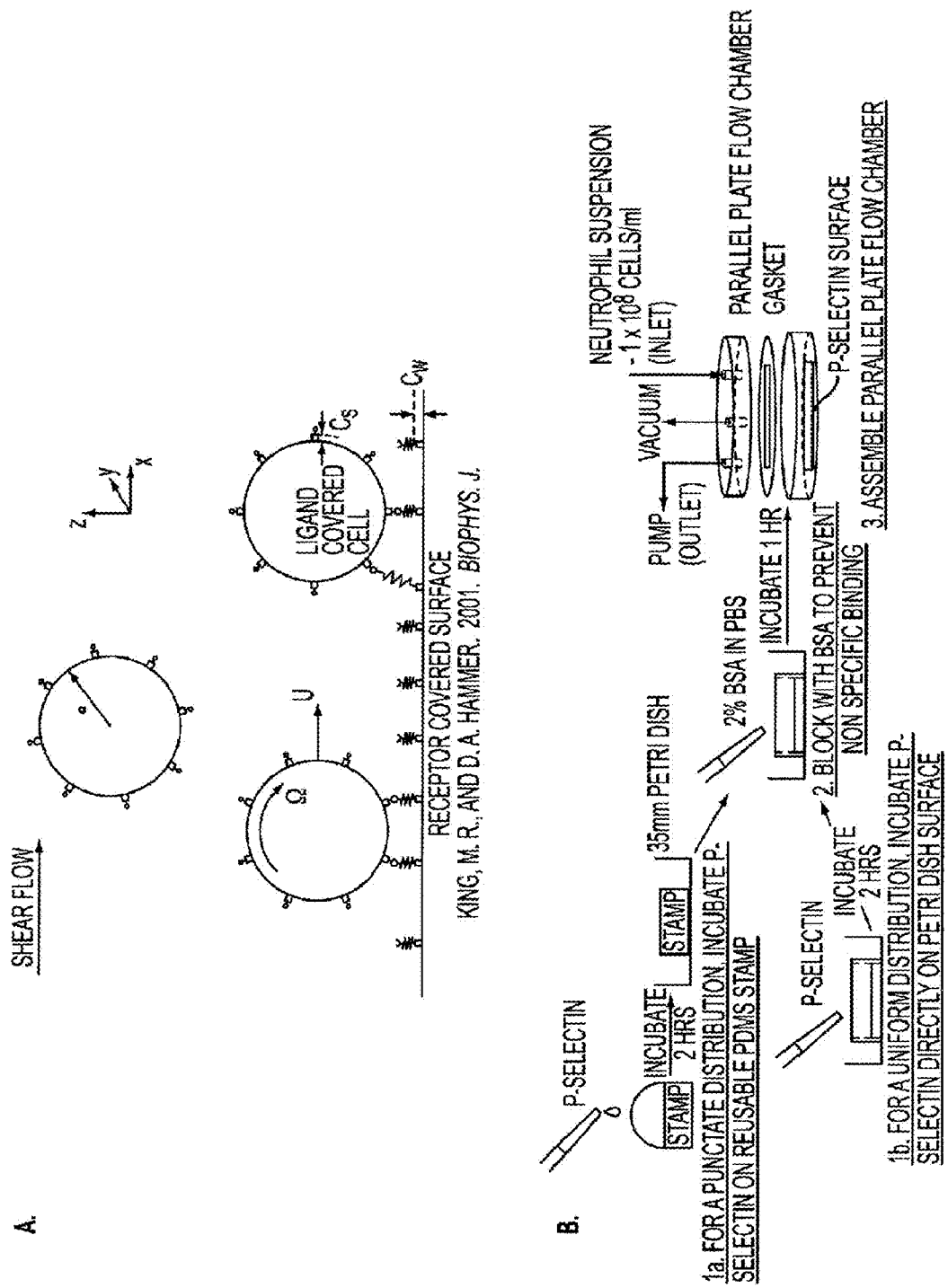
FIG. 3 is a description of experimental methods used to study the flow of cells in vitro. (A) is a schematic diagram of a cell rolling on a surface with attached adherent molecules. (B) is a schematic of a protocol for preparing an experimental surface.

Once the MAD simulation was validated, the model was tested with observations of leukocyte-endothelial interactions in intact venules of an appropriate animal model of inflammation. P-selectin-mediate rolling is visualized in post-capillary venules of diameter 22-37.mu.m in cheek pouch of anesthetized hamsters using intravital microscopy. Rolling velocity was found to be a strong function of the center-to-center separation distance to the nearest cell, and also to correlate strongly with the number of nearby cells. These effects are beyond that attributable to variations in vessel width or molecular expression along the length of the vessel. Adherent leukocytes is observed to provide a nucleation site precipitating further adhesion events of free-stream cells, confirming that the hydrodynamic recruitment mechanism first demonstrated in simulations and cell-free experiments is indeed an important mechanism for cell capture. These results agree with their previous theoretical considerations of the flow field induced by multiple nearby cells. FIG. 2 shows representative results from the MAD simulation, in vitro cell-free experiments and in vivo measurement of rolling velocity, demonstrating the excellent agreement between the engineered system and the animal inflammation model.

The modification of the surface expression of CD34+ cells can be achieved by treating cells with NPPB (a broad-spectrum Cl channel inhibitor). Short exposures to NPPB have been shown to decrease L-selectin levels by a factor of 2. The inventors have successfully used this method to decrease the L-selectin expression on mature leukocytes, and furthermore, preliminary adhesion experiments have confirmed that these changes in L-selectin expression significantly affect both average rolling velocity and rolling flux on sLeX.

In one preferred embodiment of this invention, this chemical modification, immobilization of NPPB on the wall of a flow chamber, alters the adhesion of this subclass of HSPC (Hematopoletic stem and precursor cells) and alters the trafficking behavior of these cells. These results can be adapted to other surface-modifying or differentiation reactions.

In another preferred embodiment of the invention, the perfused cell suspension leaves the flow chamber and is collected into the pump syringe and then stored after fixation until such time as the outlet stream can be tested by flow cytometry to determine the extent to which the L-selectin expression of CD34+ cells has been successfully altered. The invention can be tested and optimized with dilute suspensions of CD34+ cells alone, followed by test mixtures of CD34+ and whole blood.

Selectins are proteins that HSCs and white blood cells bind or stick to transiently. CD34+ stem cells are the immature stem cells and have maximum stem cell activity, and have been shown to roll more efficiently (or slower) than CD34− stem cells, which are the more committed or differentiated cells. Red blood cells and platelets do not roll on selectin, while white blood cells and some tumor cells exhibit rolling. Examples of selectins are P-selectin, L-selectin and E-selectin.

The technology aims at exploiting the differential rolling abilities of these cells and accordingly designing a flow chamber coated with an optimum distribution of selectin, molecules that can filter out the PBSCs (peripheral blood stem cells) from the remaining blood components.

United States Patent Application US20040191246, "Process For In Vivo Treatment of Specific Biological Targets in Bodily Fluid," addresses the need for a device capable of sorting and separating useful cell types based on their biological properties. The patent application describes an invention comprised of "a process for the in vivo treatment of the bodily fluid of a biological organism wherein said organism is implanted with a device, the bodily fluid is brought into contact with a binding agent within the device and the flow velocity of at least one of the cellular components of the fluid is reduced."

The device proposed in this application improves upon the device described in US2004/0191246 by adding the capability to manipulate adult stem cells flowing in the peripheral blood. The basic premise of the device is to transiently capture flowing adult HSPC from the blood, and while the cells are in close contact with the surface, to modify the surface receptor presentation of the captured cell so as to modify its homing properties. In this manner, stem cells may be redirected in the body. Examples of improvements beyond the scope of US2004/0191246 in the present case include adding a recycle stream, and assembling multiple stages of flow chambers in series.

One embodiment of the device, which can be implanted in a human or an animal, or used ex vivo, can specifically modify targeted cells including cancer cells and early progenitor cells as described.

In one preferred embodiment of the current invention, cells in the circulating blood are (i) transiently captured, (ii) chemically modified on their surface to alter their adhesive properties, and (iii) released into the bloodstream while retaining their viability. This embodiment has particularly preferred application in the formation of an implantable device for the selective neutralization of the tumor forming potential of circulating metastatic cancer cells. The implantable device preferably contains a chamber whose surfaces are coated with an adhesive molecule for cancer cells, preferably selectin, and a molecule that neutralizes or kill cancer cells, preferably TRAIL, Fas ligand, or chemotherapeutic drug. Here the adhesive molecule causes the cancer cells to slowly roll along the surfaces of the chamber, while the TRAIL (or other molecules that neutralizes cancer cells) neutralizes the tumor-forming capacity of the circulating cancer cells before they are released from the flow chamber back into the circulation.

Because the TRAIL (or other molecules that neutralizes cancer cells) molecule is attached to the device surface and not freely injected into the bloodstream, it produces minimal TRAIL-related side effects and contributes to an improved quality of life for the patient.

The device, once implanted in a patient, screens circulating blood and neutralize the tumor forming potential of circulating metastatic cancer cells without interruption of blood flow. This technology has the potential to provide significant benefit as an adjunct cancer therapeutic to prevent the spread of metastatic tumors, which have a significant impact on cancer related mortality and degradation of quality of life. Furthermore, this technology has the potential to be tuned for specific cancers to increase its effectiveness by customizing the geometric constraints, molecular interactions, and applied therapeutic agents to optimize potency against specific cancer types.

In another preferred embodiment, the device here described contains a recycle stream. Where part of the outlet stream from the device is recycled back to the inlet stream. This effectively increases the inlet concentration of the desired cells, thus improving the concentration of the outlet stream.

In yet another preferred embodiment, the device here described contains a multiple stages of flow chambers in series. In this case, at least two devices are connected in series, where the outlet stream of one device feeds into and inlet of the next device. Each subsequent device further concentrates, separates, and/or purifies the desired cells.

One preferred embodiment of this device consists of a glass microcapillary network with an inner coating of adhesive molecules in whole or part of the network. Because the binding is not permanent, the bonds formed can dissociate quickly allowing the bound cell to "roll" when subjected to a flow stream in the microcapillary. The microcapillary system, also referred to as microfluidic or micro-total analysis systems (.mu.TAS), are commonly known in the art and are disclosed in detail in U.S. Pat. Nos. 6,692,700 to Handique et al.; 6,919,046 to O'Connor et al.; 6,551,841 to Wilding et al.; 6,630,353 to Parce et al.; 6,620,625 to Wolk et al.; and 6,517,234 to Kopf-Sill et al.; which are incorporated herein by reference. The microcapillary network is especially useful in cell separation, concentration, and/or purification of small volume samples at high throughput.

Reproducible test data produced by the inventor shows that a precise combination of multivalent P-selectin chimera together with anti-CD34 antibodies is able to increase the difference in rolling velocity between HSCs and mature leukocytes from zero to a factor of two. This difference in rolling velocity, with the HSCs rolling consistently slower over a wide range of physiological wall shear stresses (1-10 dyn/cm2) will serve as the basis for a high-throughput, flow-based cell separation process.

In one preferred embodiment of the current invention, a parallel plate flow chamber device, functionalized with a P- and E-selectin-presenting surface to support rolling interactions of the HSPC and mature hematocyte suspensions is connected to the circulation of a patient.

Previously, the applicant has used a system to study leukocyte adhesion focused on the cell-free assay, where leukocyte and endothelial adhesion molecules are reconstituted in a synthetic system consisting of polymer microspheres (model leukocytes) presenting sLe.sup.x, PSGL-1, or other selectin-binding ligand (Brunk et al., Biophys. J. 72:2820-2833, 1997; and Rodgers et al., Biophys. J. 79:694-706, 2000) which serves as a model for the construction of the current device. The lower surface of a parallel plate flow chamber is coated with P-selectin, E-selectin, L-selectin, or other adhesion molecule constitutively expressed by the endothelial cells that line blood vessels. The cell-free assay has been shown to exhibit noisy rolling behavior similar to leukocytes interacting with intact post-capillary venules. Cell-free experiments have been useful in identifying the physiological role of the myriad of receptors and counter-receptors present on the surface of blood and endothelial cells (Goetz et al., Biophys. J. 66:2202-2209, 1994). The applicant has published on these experimental techniques in several papers (King et al., Langmuir. 17: 41394143, 2001; King et al., Biophys. J. 81:799-813, 2001; and King et al., Proc. Natl. Acad. Sci. USA. 98:14919-14924, 2001).

Coating of the rolling surface or chamber may be accomplished with a protocol such as follows. The rolling surface is incubated with concentrations of soluble P- or L-selectin (R&D Systems) ranging from 2-20.mu.g/mL for 2 h. The coated surface will be assembled into a commercially available adhesion flow chamber (Glycotech), and connected to a computer-controlled syringe pump (New Era Systems). Isolated HSPC will be suspended in PBS buffer with 1 mM calcium ion and 0.5% HSA to minimize nonspecific adhesion with the surface. A mixture of cells containing CD34+ cells is used in the cell separation, and fed into the flow chamber with shear rates ranging from 50-1000 s.sup.−1. The cells not containing CD34, which have been shown to exhibit weaker and more transient adhesion to selectin-presenting surfaces, will preferentially pass first through the flow chamber system and exit to the outlet stream. Preferably, the cell mixture contains calcium because calcium ion is necessary for selectin to adhere to its carbohydrate ligand. At certain point after flow is initiated, the inlet solution is switched to calcium-free media which "releases" the CD34+ cells from the selectin surface, and these cells will be mostly contained within the final fractions of outlet suspension. The precise time at which to switch perfusion media is not yet known. However, assuming an average CD34+ rolling velocity of 20.mu.m/s at a shear rate of 200 s$^{-1}$ and a usable selectin surface length of 13.5 mm, then to minimize the number of CD34+ cells exiting into the calcium-containing fractions, a switchover time of .about.14 min. should be used. This switchover time will be optimized to achieve the maximum separation of cells, by performing computer simulations of the separations experiment as described below. The relative concentrations of CD34+ and CD34− cells can be assessed via flow cytometry, by first treating the cell suspensions with antiCD34 primary antibodies (R&D Systems, Rockville, Md.) and fluorescent secondary antibody (Molecular Probes).

In yet another embodiment of the present invention, separation of CD34+ cells from whole blood mixtures is achieved using a combination of selectin and anti-CD34 antibody adhesion. This includes separation of CD34+ and CD34− HSPC based on differences in selectin-mediated rolling.

In another embodiment of this invention, a variation on, and extension of, the concept of separating cell populations that differ in CD34 surface presentation but are alike in physical characteristics, mixed HSPC populations in whole blood suspensions are isolated via selectin-mediated rolling from whole blood. In this case it will be necessary to coat the flow surface with both P-selectin (or L-selectin) and immobilized hapten-conjugated anti-CD34 monoclonal antibody (e.g. QBEND/10, IgGl, 0.5.mu.g/10.sup.6 cells). Note that the selectin molecule is necessary since it has been demonstrated that antibody molecules alone are insufficient to capture cells from the freestream, most likely due to the lower rate of bond formation compared to the selecting. In this case common, fully differentiated leukocytes will slowly roll through the flow chamber due to selectin interactions, however, the more immature HSPC will be completely arrested due to antibody interactions. Once the mature cells are flushed from the flow chamber, the captured HSPC must be released with a final elution step.

A preferred embodiment of this invention consists of flow chambers constructed such that, instead of producing a well-defined parabolic velocity profile, would better represent the complex sinusoid flow in the bone marrow.

In one preferred embodiment, a flow chamber containing adhesion molecules captures immature HSPC and adhesively retains them close to the lower wall for sufficient time to chemically modify the surface of the cells before they are released to the bulk flow at the downstream edge of the functional flow chamber.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

EXAMPLE 1

In order to establish protocol without sacrificing precious HSPCs, we utilized a model system where $CD34^+$ KG1a cells represented the HSPCs and $CD34^-$ HL60 cells represented the $CD34^-$ ABM cells. The KG1a/HL60 model was used to determine an optimum P-selectin concentration for subsequent HSPC experiments. We initially found that KG1a and HL60 cells rolled at very similar velocities at all P-selectin concentrations tested so, based on the data from Eniola et al. (2003), we co-immobilized anti-CD34 antibody together with the P-selectin and found that, at 0.5 $\mu$g/ml P-selectin and 40 $\mu$g/ml anti-CD34, there was a significant difference between the rolling velocities of the two cells (FIG. 6A). This more closely represented previous findings that HSPCs tend to roll slower than $CD34^-$ cells on selecting, which was further confirmed by our own HSPC/$CD34^-$ ABM cells experiments using 0.5 $\mu$g/ml P-selectin (FIG. 6B). The presence of the antibody had little effect on the rolling velocity of the ABM cells so it was not used in subsequent experiments using ABM cells.

EXAMPLE 2

Cell retention as a function of time was also determined for both cell models at a shear stress of 3 dyn/$cm^2$ for 10 minutes. Cells were initially loaded over the entire surface and allowed to settle for 40 s for KG1a/HL60 cells, and 2 minutes for ABM cells, based on the Stokes settling velocity of the cells of interest. We found that KG1a Cells had a higher accumulation than HL60 cells on the P-selectin/antibody surface and similarly, there was higher retention of HSPCs than $Cd34^-$ ABM cells on the P-selectin surface (FIG. 7).

We were able to use this data to predict and confirm with experiments that there would be significant enrichment of KG1a cells for KG1a/HL60 cell mixtures ranging from 10-50% KG1a cells. Predictions using physiologic ABM concentrations of 1-5% HSPC showed more modest improvements and were not confirmed experimentally (FIG. 8).

Figure 9:
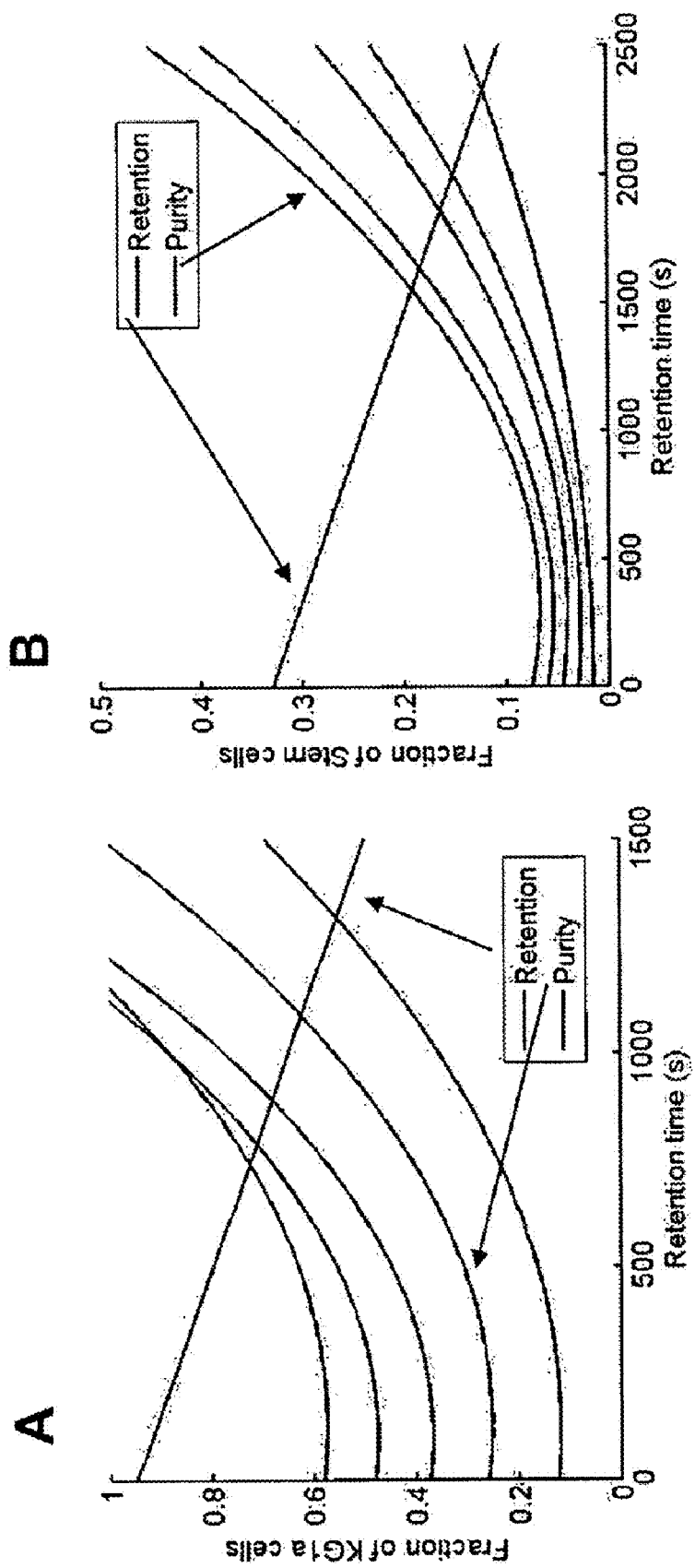
FIG. 9 show determination of optimum enrichment time. While optimum enrichment should take between 10-25 minutes for KG1a cell mixtures (A), we can expect optimum enrichment to take 25-45 minutes for HSPC cell mixtures (B).

We extended the prediction to determine the length of time for optimum enrichment, i.e., the time for purity and retention to be equal. We determined that while optimum enrichment would take less than 25 minutes with KG1a/HL60 cell mixtures, it would take over 30 minutes for modest enrichment of HSPC (FIG. 9).

EXAMPLE 3

Figure 10:
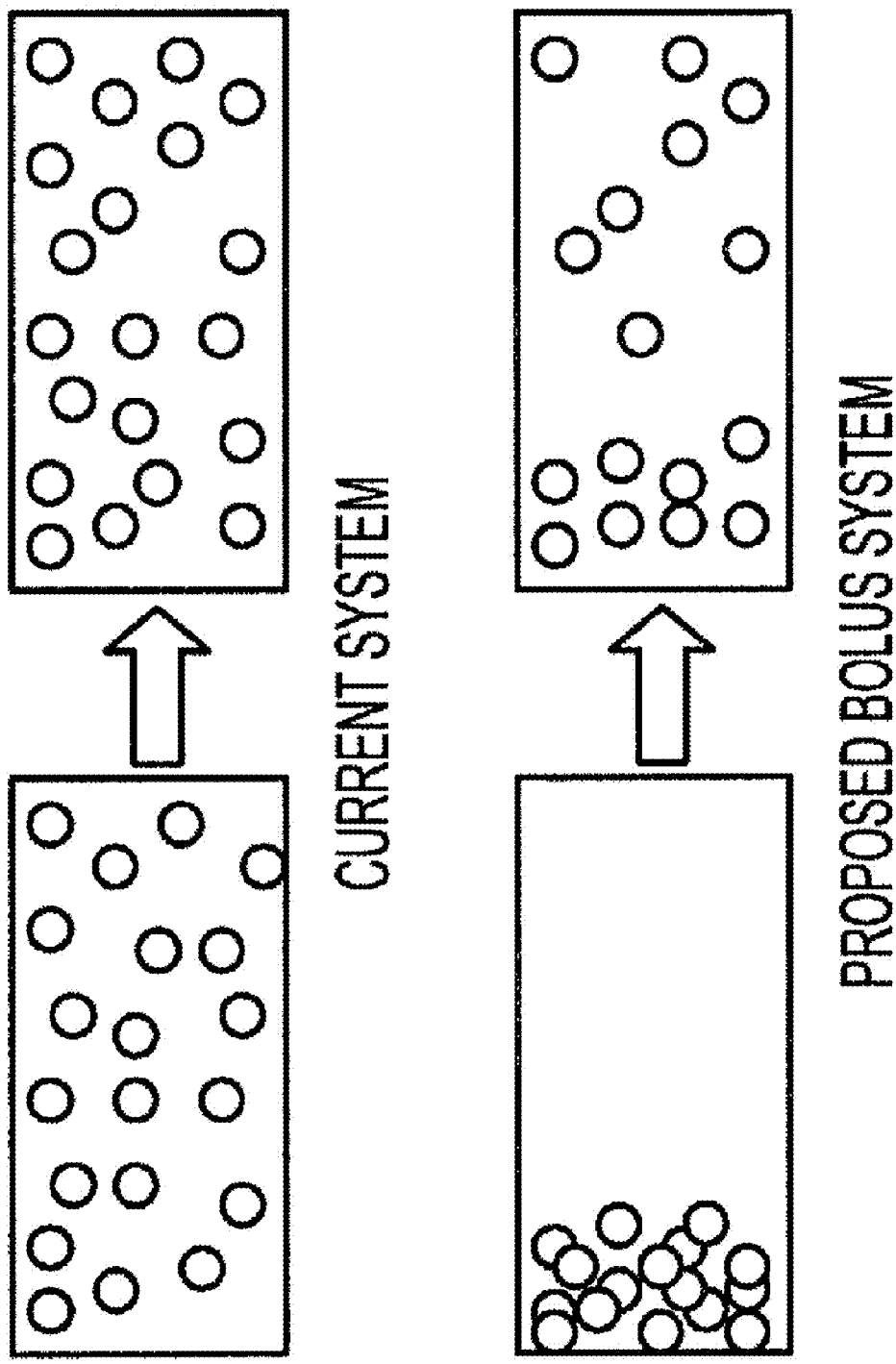
FIG. 10 is a picture depicting better separation for loading of a small portion of the rolling surface. Loading a small portion of the surface instead of the whole surface may ("bolus" system) be better for separation.

As mentioned before, we established conditions for determining the effectiveness of our system based on recommendations from Johnsen et al (1999) —Cell purity >80-90%, Cell retention >50% and optimum separation within 30 minutes. It was evident that our current system needed significant improvements to achieve these preliminary goals, so we investigated whether our cell loading system was optimized for this type of separation. Instead of loading the entire surface, only a small portion (<10%) of the surface would be used for the initial cell loading step so that the device could make use of the natural tendency of the cells to separate based on rolling velocity (FIG. 10).

Figure 12:
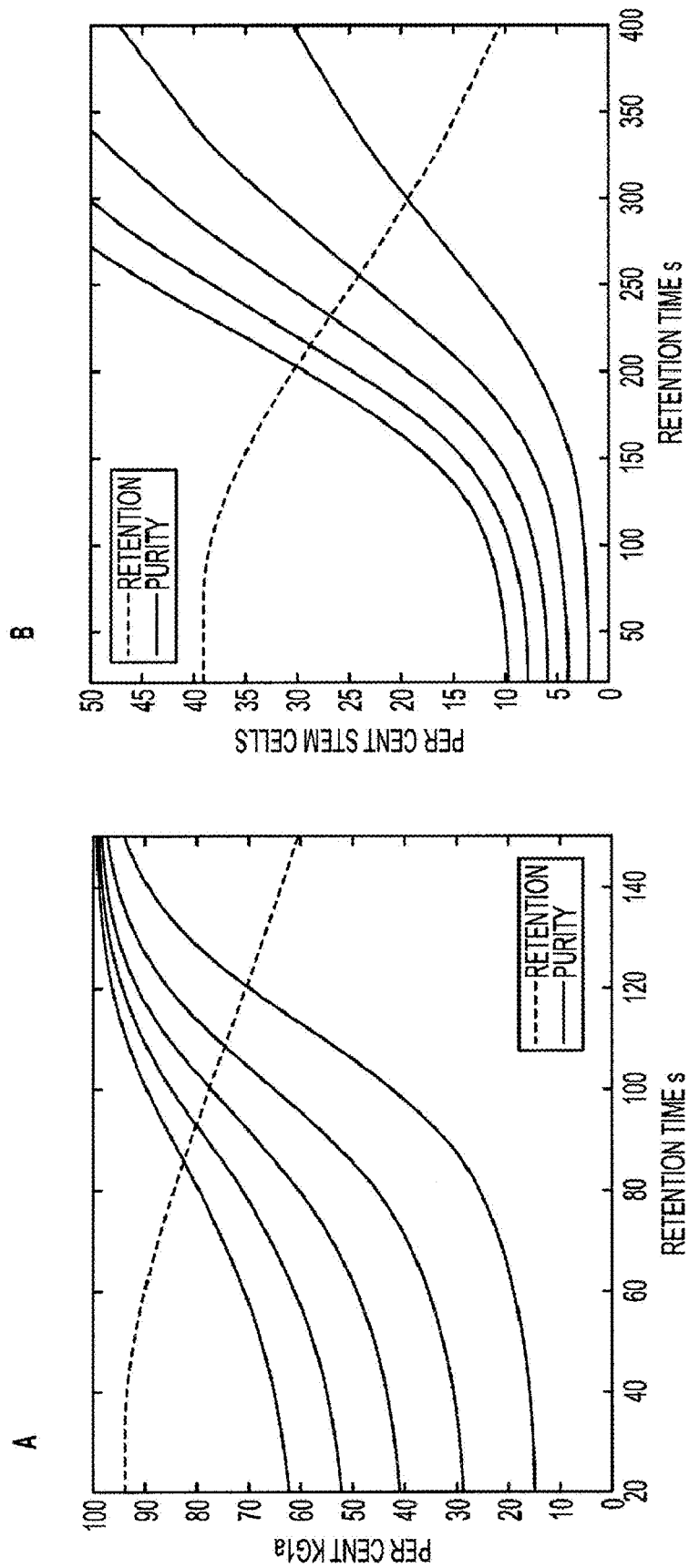
FIG. 12 predicts the separation abilities of a 'bolus' cell loading system. Optimum separation should be possible within 5 minutes for all cell mixtures on a 1 mm long functional surface. Increasing the length of the functional surface proportionally increases the cell retention time and hence the tie for enrichment.
Figure 13:
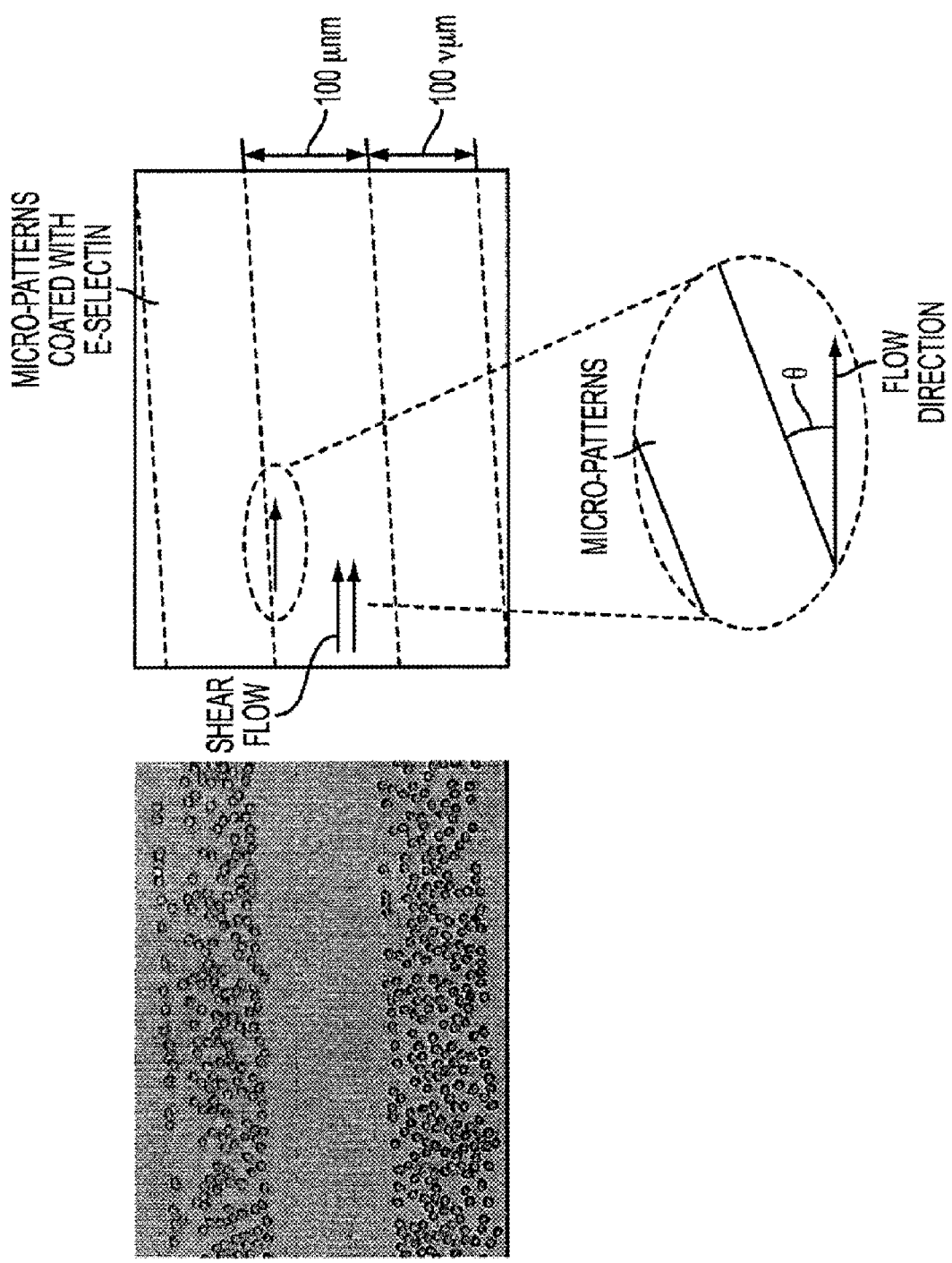
FIG. 13 shows a micropattern (punctated pattern) of adhesion molecule consisting of repeating linear stripes.

We used an exponentially modified Gaussian (EMG) distribution to describe the velocity distribution of cells at 3 dyn/$cm^2$ (FIG. 11). The peak to peak resolution for HL60/KG1a cells and HSPC/$CD34^-$ ABM cells was about 0.4, corresponding to about 40% cross contamination. Coupled with the cell retention data obtained at t=0 s, we were able to predict the optimum cell enrichment possible with 10-50% KG1a cell mixtures and 1-5% HSPC cell mixtures, assuming a functional length of 1 mm (FIG. 12). In both cases, optimum cell separation should be possible within 5 minutes with significant improvements in purity over our current loading system.

Since we envision the final device as a multistage device, we expect even higher purities and cell recovery >50% should be likely since detached $CD34^+$ cells can be recaptured in subsequent stages. Our preliminary experiments and prediction confirm that cells can be separated based on differential rolling velocities, and while we are limited by the current design of our experimental system, proper design and manufacturing techniques could make this device a reality. We continue to investigate new ways of improving the theoretical effectiveness of the system and search for alternative experimental methods for testing our separation predictions.

EXAMPLE 4

Figure 14A:
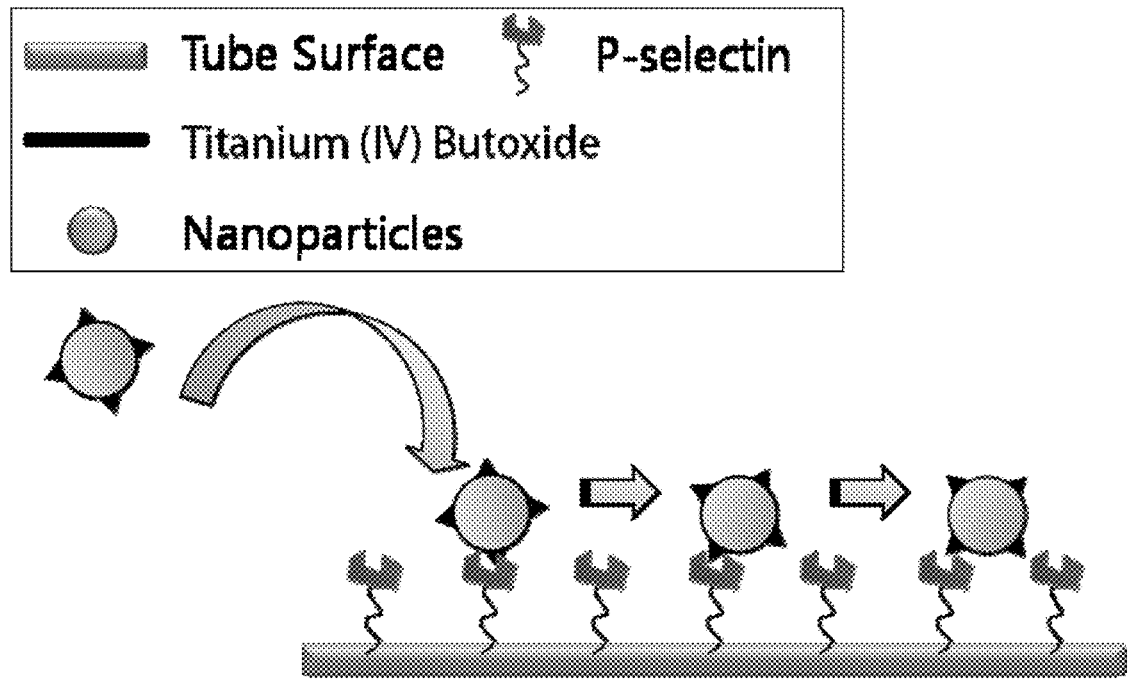
FIG. 14a shows a representation of control tube containing only P-selectin and rolling cells.
Figure 14B:
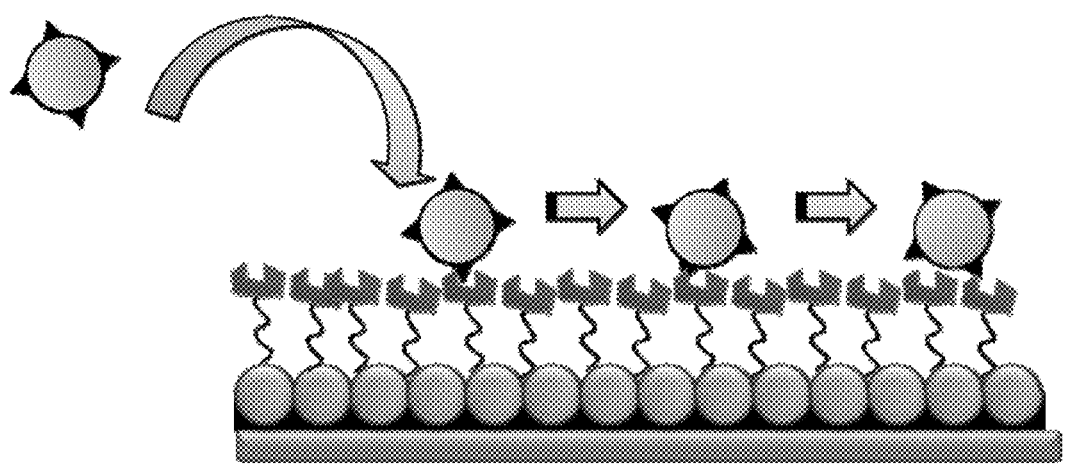
FIG. 14b shows a representation of a nanoparticle-coated (NP)-tube creating increased binding surface for P-selectin.

In this example, both organic and inorganic adhesive layers were used to form a colloidal silica nanoparticle (NP) interface layer as a means to improve cell binding (FIG. 14). Silica NP presence on modified surfaces was evaluated by atomic force microscopy (AFM). Immunofluorescence microscopy of P-selectin was used to assess the surface quantity of P-selectin. Acute myeloid leukemia cell line (KG1a) was used for cell adhesion assays due to their high expression of P-selectin ligand glycoprotein-1 (PSGL-1), which mediates cell rolling on P-selectin both in vitro and in vivo.

Materials and Methods

Preparation of KG1a Cells

KG1a (acute myeloid leukemia) cells were cultured in RPMI media (Mediatech, USA) with 1% L-glutamine (Mediatech, USA) and 10% fetal bovine serum (FBS) (Atlanta Biological, USA). For experiments, cells were isolated from the media and added to Hank's balanced salt solution (HBSS+) (Invitrogen, USA) to a final concentration of $1 \times 10^6$ cells/mL.

Preparation of Nanoparticle-Coated Microtube Using Poly-L-Lysine

Poly-L-lysine $(PLL)_n$ (0.1% w/v, in water; Sigma-Aldrich, USA) solution was diluted to 2:8 with deionized water. The solution was incubated inside the Micro-Renathane tubing (MRE-025, ID 300 um, length 50 cm; Braintree Scientific, USA) for 5 minutes at room temperature. $SiO_2$ nanoparticles (NPs) dispersed in methanol (10-15 nm, 30-31 wt % $SiO_2$, pH 4; Organosilicasol™, Nissan Chemicals, USA) was pumped through the tube and incubated for 3 minutes at room temperature. In order to prevent tube clogging, the tube was flushed with methyl alcohol (Mallinckrodt Chemicals, USA). The tube was stored at room temperature overnight for curing.

Preparation of Nanoparticle-Coated Microtube Using Titanium (IV) Butoxide

Titanium (IV) butoxide (Tyzor TBT®, DuPont™, USA) solution was diluted to 2:8 with butyl alcohol (Mallinckrodt Chemicals, USA). The solution was incubated within Micro-Renathane tubing (MRE-025, ID 300 um, length 50 cm). $SiO_2$ NPs dispersed in methanol (10-15 nm, 30-31 wt % $SiO_2$, pH 4) were pumped through the tube immediately and incubated for 1 minute at room temperature. The tube was washed with methyl alcohol to prevent clogging, and then stored at room temperature overnight for curing.

Microtube Preparation for Cell Capture and Rolling

Recombinant human P-selectin/Fc Chimera (P-selectin; R&D Systems, USA) at a concentration of 5 ug/ml in phosphate buffered saline (PBS; Invitrogen, USA) was incubated inside the tube for 2 hours at room temperature. After washing the tube with PBS, the tubes were incubated with 5% bovine serum albumin (BSA; Sigma-Aldrich, USA) to block non-specific binding. HBSS+ was pumped through the tube to activate the coated P-selectin. For each experiment, 4 tubes were prepared following the same procedure: P-selectin tube, PLL tube, NP-coated tube, and P-selectin+NP-coated tube.

Cell Capture and Rolling Experiment

Tubes were placed on the stage of an Olympus IX-81 motorized inverted microscope (Olympus America Inc. USA) attached to a CCD camera (Hitachi, Japan). A syringe pump (New Era Pump Systems) was used to control the flow rate of the cell suspension. All images and videos were recorded on high-quality DVD+RW discs for offline analysis.

Fluorescence Microscopy

Tubes were prepared with P-selectin and blocked with 5% BSA, in the same manner as described above. The tubes were incubated with mouse anti human CD62P-Alexa 647 mAb (Serotec, USA) for 2 hours. An Olympus IX-81 microscope with Cooke Sensicam QE camera and IP Lab software were used to record the fluorescent images under TRITC mode. Image analysis was done using ImageJ (NIH) and Excel (Microsoft). The background fluorescent of the tube has been subtracted from each data.

AFM Analysis

AFM images were taken of both NP and control (adhesive only) surfaces. Both surfaces were prepared by steps shown previously on glass slides and washed thoroughly with distilled water.

Data Analysis

Videos from DVD+RW discs were reformatted to 640×480 pixels at 29.97 fps with ffmpegX software. Rolling velocities of cells in the tubes were acquired using ImageJ, Excel, and Matlab R2007a (Mathworks). For statistical analysis, paired t-test ($\alpha$=0.05 level of significance) was used to analyze the data where applicable. Each experimental condition was repeated twice and reported as mean±SEM values. Immobilized or rolling cells were considered captured. The definition of rolling and the method of estimating the number of cells captured in 50 cm-long tube were as previously described. Rolling cells were defined as cells rolling at <50% of the calculated hydrodynamic free stream velocity, and cells that remained stationary for more than 10 s were not classified as rolling.

Results and Discussion

AFM Analysis

Figure 15:
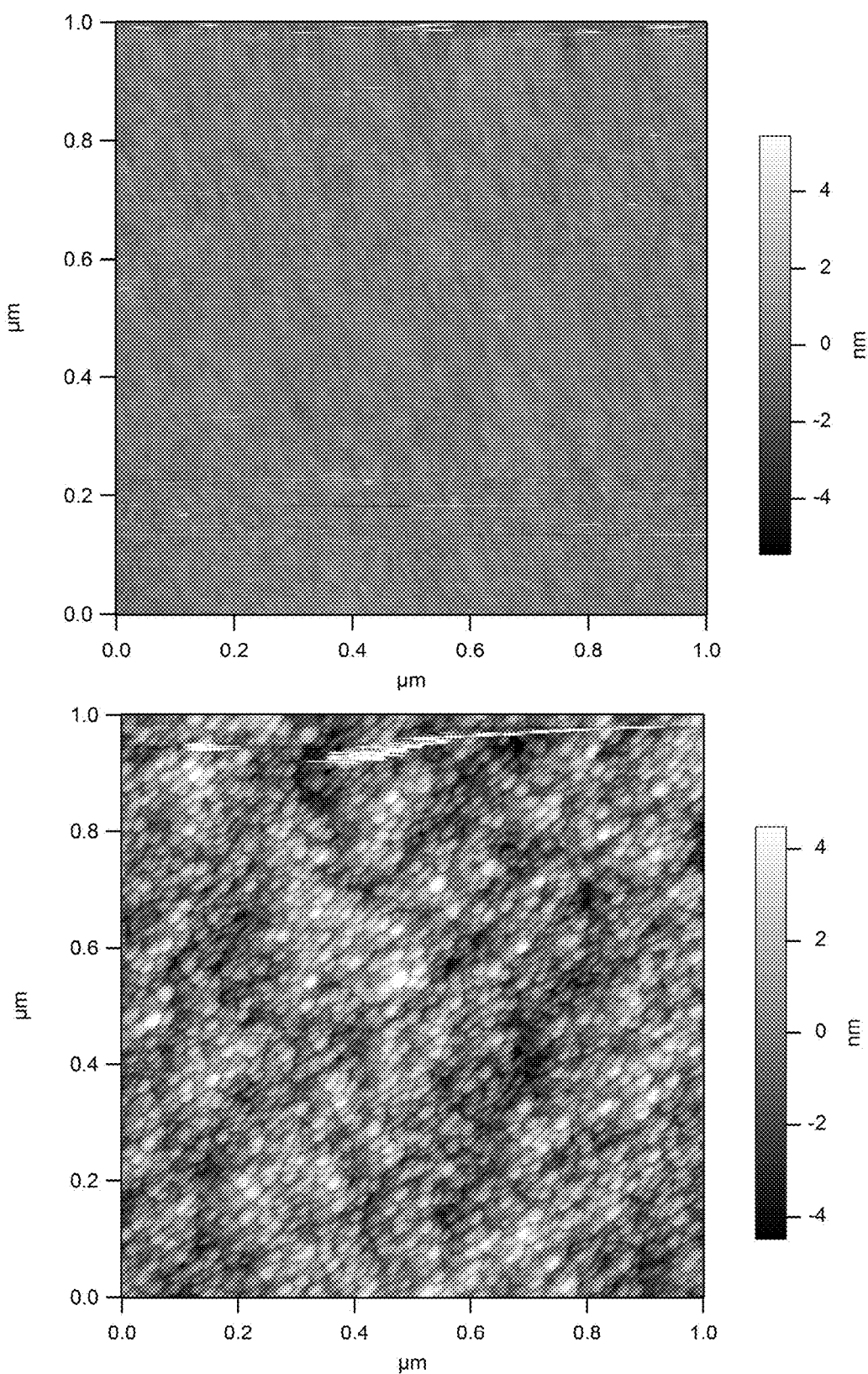
FIG. 15. Top: AFM image of control (adhesive only) surface. Bottom: AFM image of NP treated surface showing presence of approximately 15 nm silica particles.

The AFM image of NP-treated surface confirmed the presence of NPs of the expected size (15 nm) even after thorough washing (FIG. 15). In addition, the AFM image shows topography of increased surface roughness as well as surface area. The control (titanium (IV) butoxide adhesive only) surface shows no measurable roughness.

Immunofluorescence Quantification of P-selectin

Figure 16:
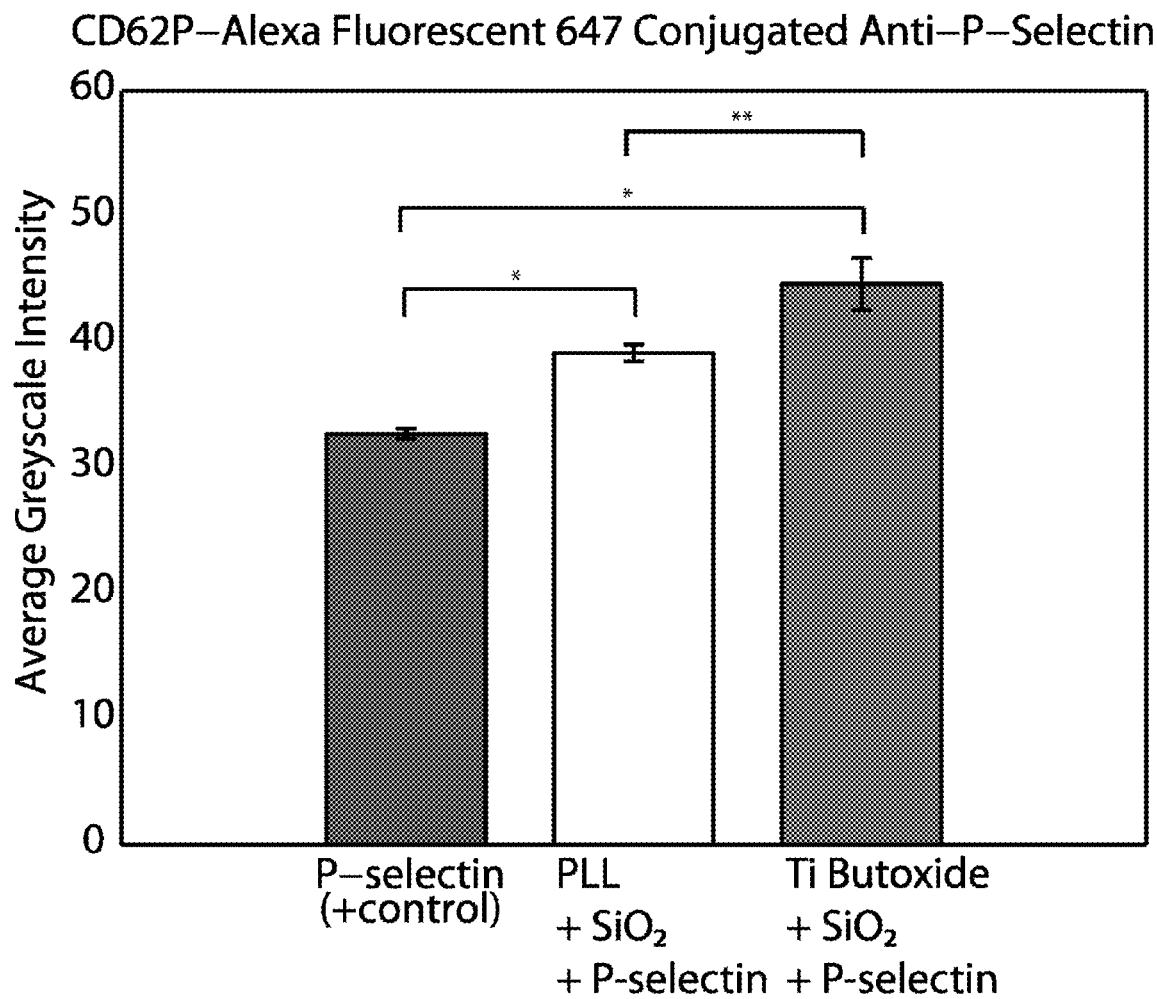
FIG. 16. The average grayscale intensity of Alexa fluorescent 647 conjugated anti-P-selectin. The background fluorescent of the tube has been subtracted from each data. Both NP-coated surfaces showed significantly higher intensity than the control. No significant difference was observed between the two NP-surfaces. * P<0.05; ** P>0.05.

Immunofluorescence of labeled P-selectin was used to compare surfaces and examine the NP ability to increase the surface area or quantity of adsorbed selectin. The average fluorescence intensity of CD62P-Alexa fluorescent 647 conjugated anti-P-selectin on NP-surfaces indicated significantly higher intensity than the control surface (FIG. 16). No significant difference was observed between the two NP-surfaces, suggesting that the effect is due to the increased surface area to the same degree. Though the immunofluorescence showed increased selectin adhesion, the data reveals nothing regarding the beneficial orientation that may also be acting in altered cell behavior.

Nanoparticle Coatings Using Poly-L-Lysine as an Adhesive

Figure 17:
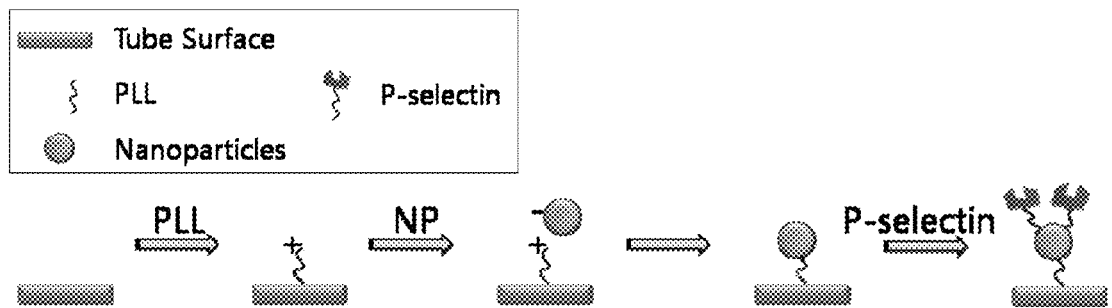
FIG. 17. The presence of PLL on the surface allows for the opportunity of electrostatic interactions between the surface and the NPs.

Once PLL is absorbed and coated onto the tube surface, the number of positively charged ammonium groups present on PLL increases, which then attract negatively charged colloidal silica via electrostatic interactions (FIG. 17). Furthermore, it is important to note that confinement can affect the diffusion coefficient of NPs which may lead to particle aggregation. Unwanted confinement that favors particle aggregation can be created as the silicate layer coating becomes thicker. Tubes can be occluded up by the buildup of NP aggregation; therefore, it is crucial to not introduce excessive NPs inside the PLL-coated tubes.

To gain a better understanding of the PLL adhesive layer, we determined the coating thickness by measuring the mass differences between completely desiccated 50 cm-long coated and uncoated tubes. Based on 10 independently conducted trials (n=10), the average mass difference equaled 0.80±0.03 mg. From this, the coating thickness was calculated to be 151±6 nm, which is in remarkable agreement with the reported random coiled (at neutral pH) PLL cylinder dimensions of ±5×300 Å=150 nm after absorption. Thus, this indicates that PLL adheres the NPs while maintaining a very thin and reproducible average coating surface.

Other advantages of PLL as the NP-coating adhesive include its biocompatibility and water solubility during processing. PLL is a polypeptide widely used in mammalian cell culture to coat culture surfaces to promote nonspecific cell adhesion and spreading. Thus, PLL is a promising adhesive that can be used when designing an implantable biomedical device in the future.

Figure 18:
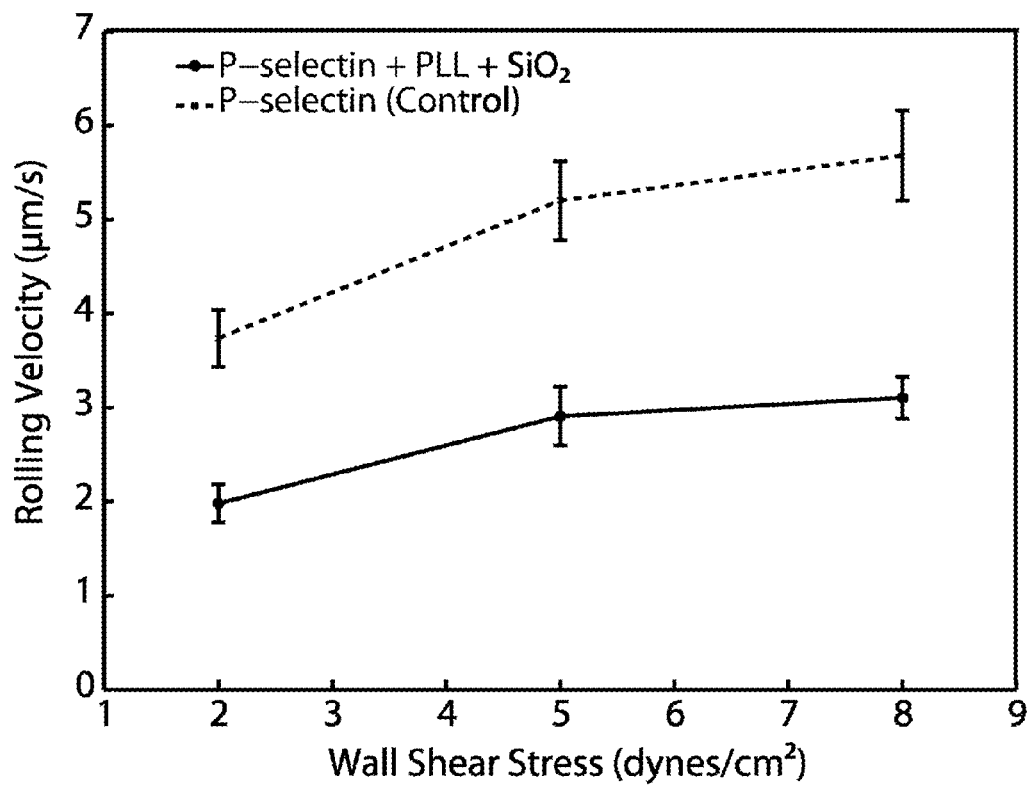
FIG. 18. Rolling studies on nanoparticle-coated and control tubes indicated a significantly slower rolling velocity of KG1a cells in nanoparticle-coated tubes. All points on each wall shear stress are significantly different (P=0.00021 (<0.05); P=0.00076 (<0.05); P=0.00018 (<0.05) respectively.).
Figure 19:
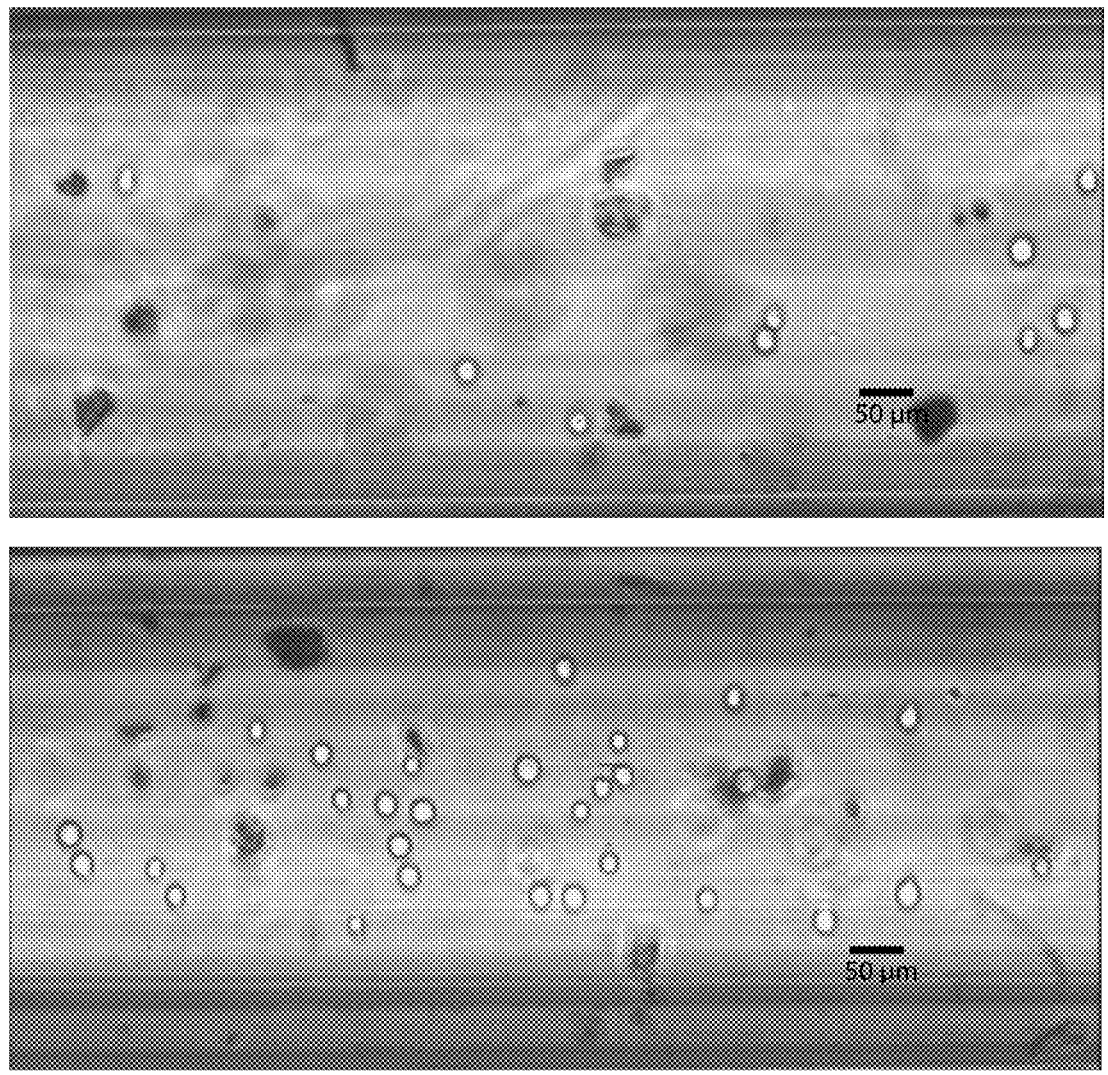
FIG. 19. Representative micrograph images captured at 8 dynes/cm2. Top: P-selectin (Control) tube. Bottom: PLL+NP+P-selectin tube.
Figure 20:
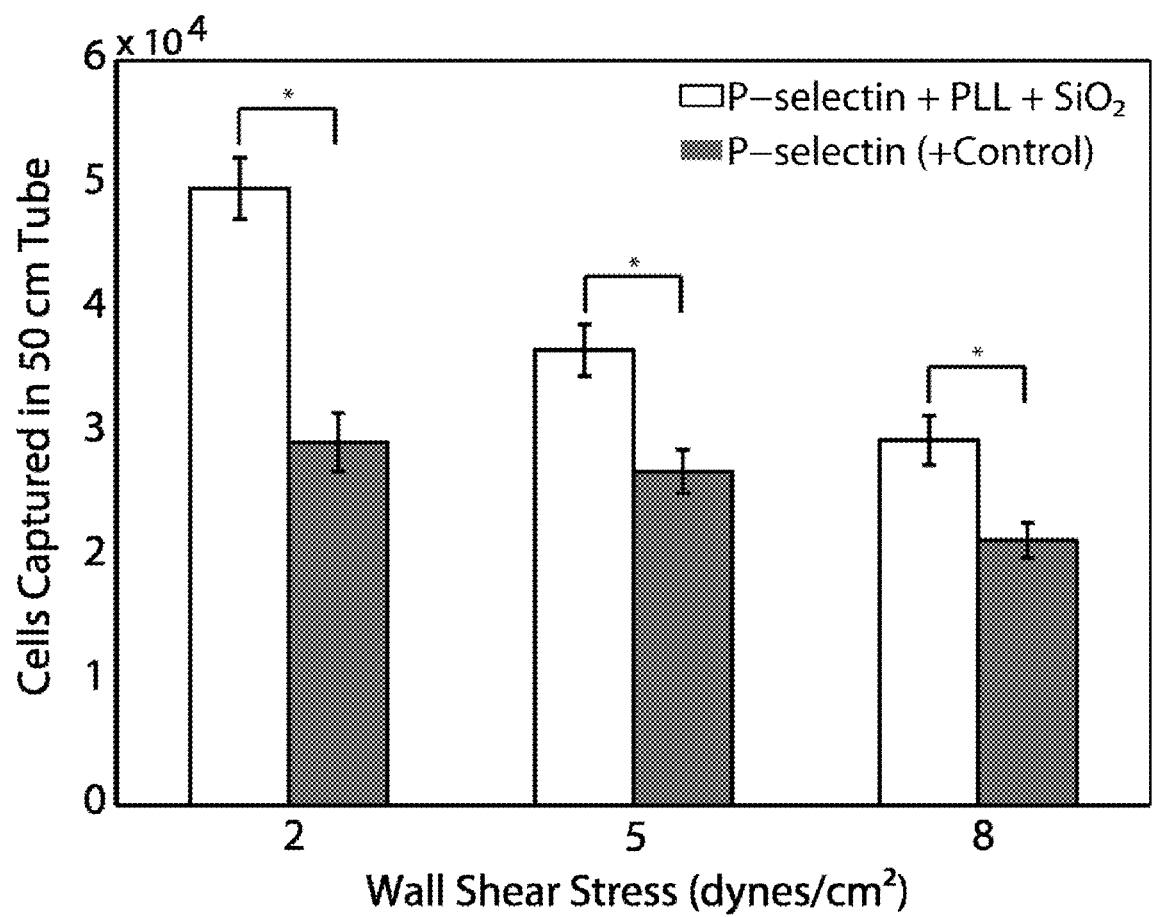
FIG. 20. The total number of cells captured in 50 cm long device under varying wall shear stresses. * P<0.05.

Characteristics of cell rolling and adhesion have been shown to be effective ways of evaluating a surface topography on the nanoscale. To study the effects of a NP interface on the capture of flowing cells, we performed rolling experiments comparing NP-coated tubes and control tubes. A significantly slower rolling velocity of KG1a cells on the NP surface synthesized using PLL and silica NPs compared to KG1a cells on the control surface was observed (FIG. 18). Over the entire range of wall shear stresses studied, the mean rolling velocities of cells were significantly slower in the NP-coated tubes (P<0.05). Similarly, the total number of cells captured in a NP-coated tube was significantly greater than with the control device lacking the NP layer (FIG. 19). At wall shear stress 2 dyn/cm$^2$, the NP-coated device showed up to a 100% increase in the total number of cells captured relative to the non-NP device (FIG. 20).

Figure 21:
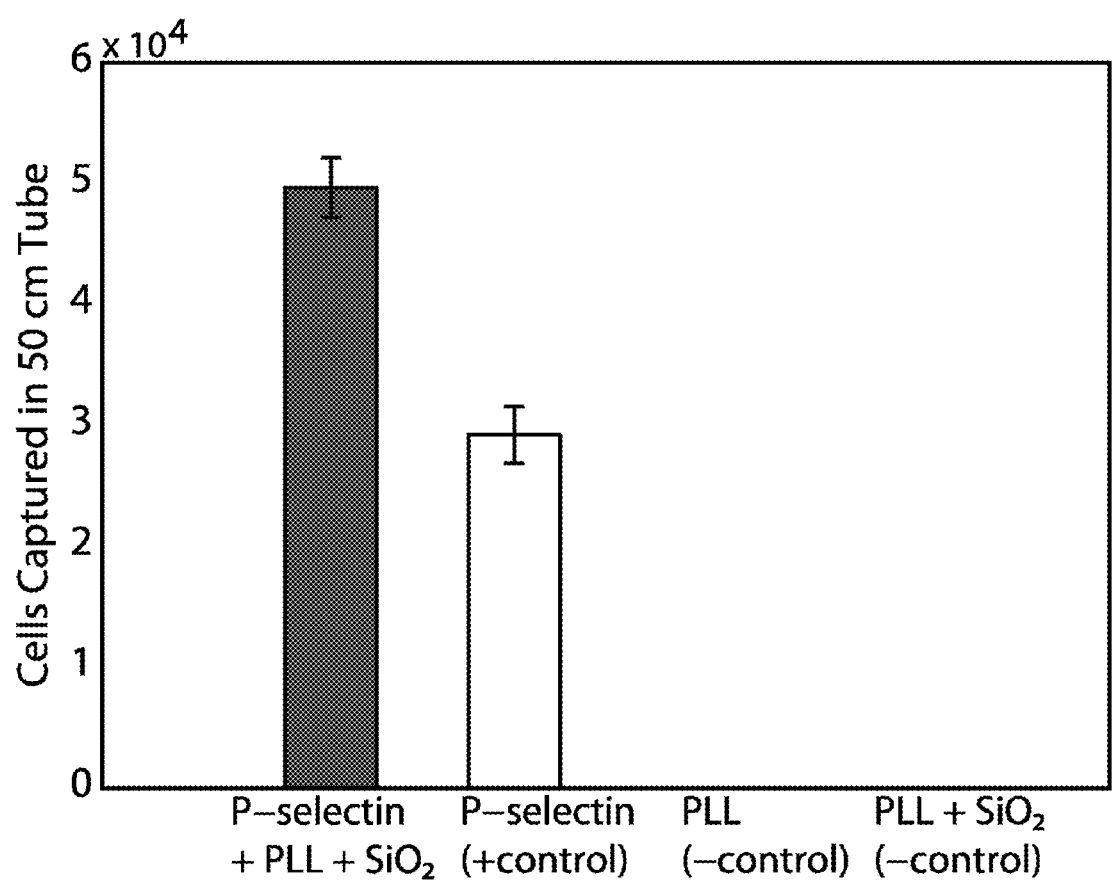
FIG. 21. The total number of cells captured on various surfaces at 2 dynes/cm$^2$. No cell adhesion was observed in negative controls.

PLL is a biological macromolecule that is used to coat synthetic surfaces to promote nonspecific spreading and adhesion of anchorage-dependent cells. To eliminate the possibility of undesired nonspecific cell adhesion to PLL that could influence the cell capture count, we conducted a similar experiment with different negative controls (no P-selectin incubations, blocked with 5% BSA) PLL, and PLL with NP-coated surfaces. Both negative control tubes showed no nonspecific cell adhesion under a wall shear stress of 2 dyn/cm$^2$ (FIG. 21). This result indicates that PLL is exclusively acting as an NP-immobilizing adhesive, and not contributing to the enhancement of cell capture though nonspecific electrostatic interactions. In addition, this supports the conclusion that the NP-coated surface with P-selectin significantly improves the cell capture from its increased surface roughness and area.

Nanoparticle Coatings Using Titanium (IV) Butoxide as an Adhesive

Figure 22:
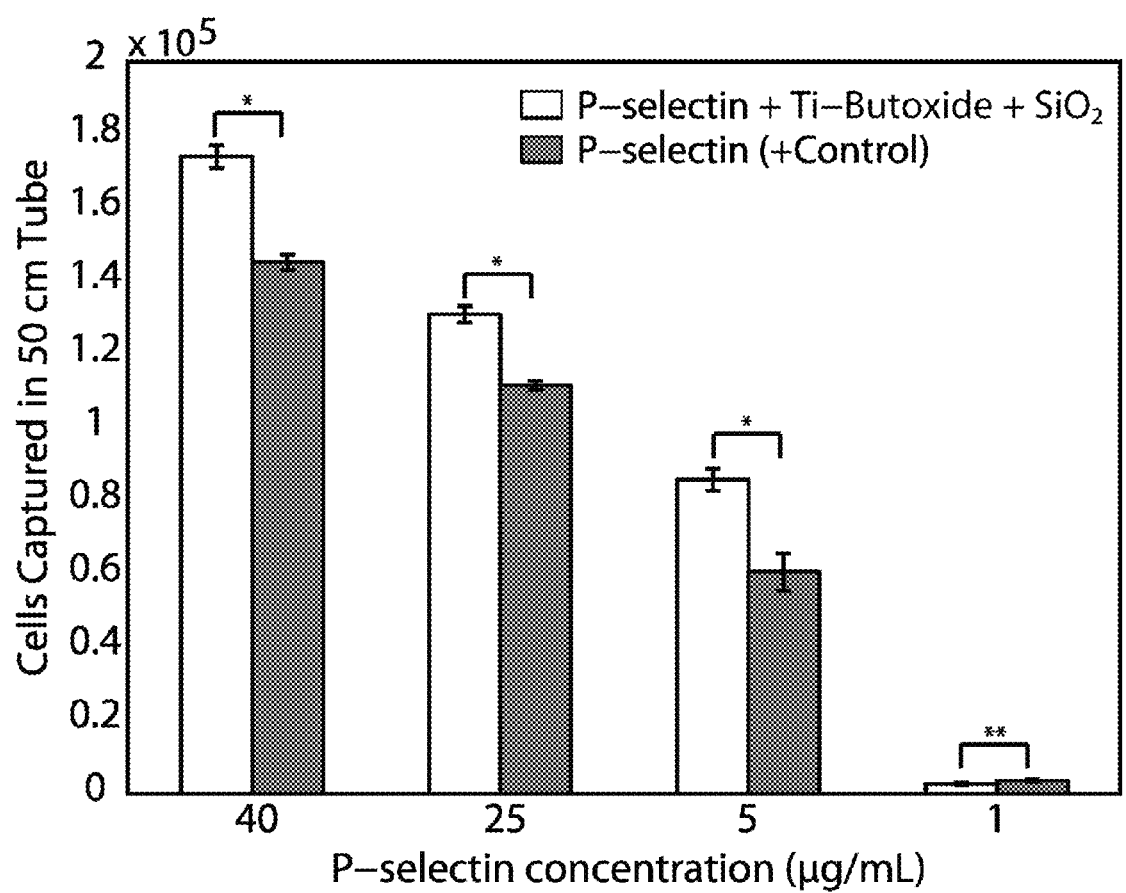
FIG. 22. The total number of cells captured in 50 cm long device under a constant wall shear stress of 2 dynes/cm$^2$. Negative controls are discussed in text above. * P<0.05; ** P>0.05.

Using acute myeloid leukemic cells (KG1a), the rates of cell and cell rolling were evaluated for cells flowing over NPs immobilized by titanium (IV) butoxide and functionalized with P-selectin. Over the entire range of P-selectin concentration studied, the presence of NPs on the interior lumen of the flow device showed significantly greater cell capture at a wall shear stress of 2 dyn/cm$^2$ (FIG. 22). Specifically, the NP surface showed similar cell capture rates as the control surface at over 1.5× less concentrated P-selectin incubation concentration. Surfaces of adhesive only (BSA blocked), as well as surfaces of adhesive and NPs (BSA blocked) were tested and showed no significant cellular adhesion or rolling.

Figure 23:
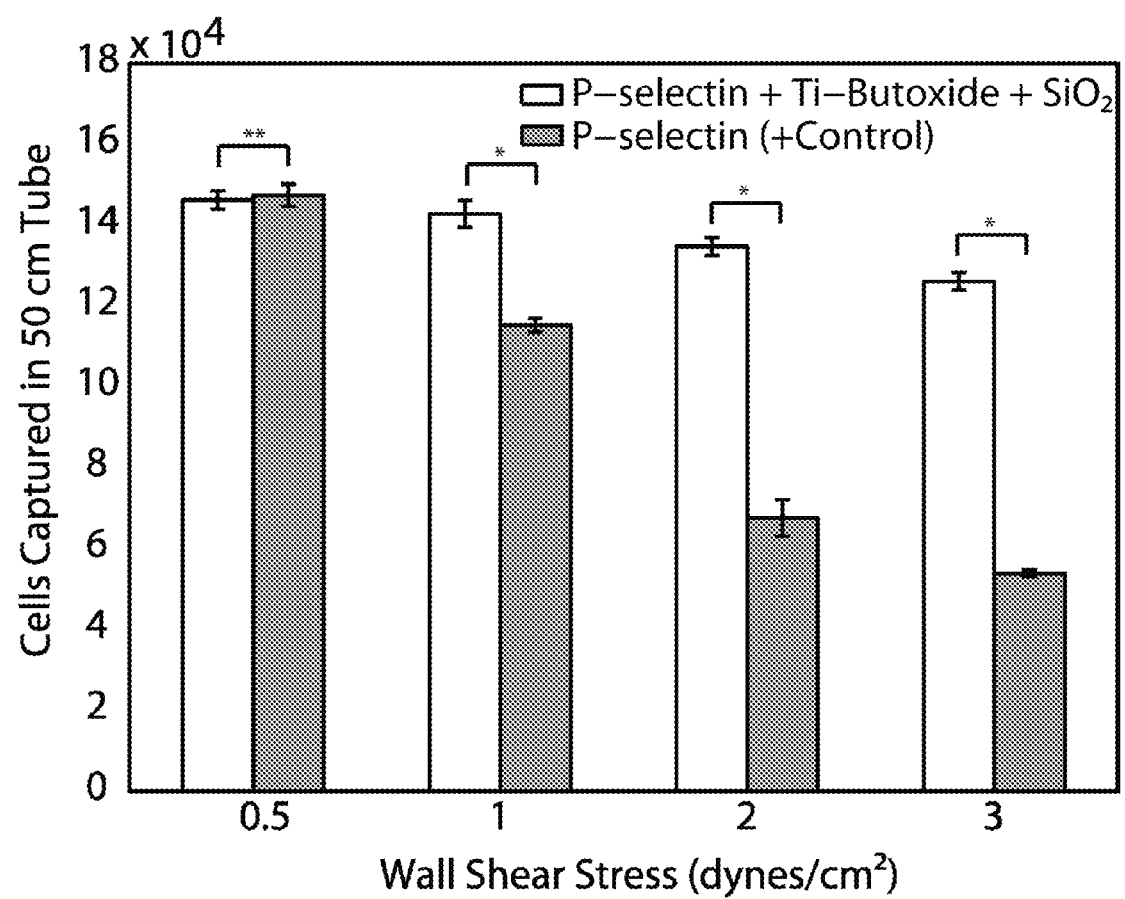
FIG. 23. The total number of cells captured in 50 cm long device under varying wall shear stresses. P-selectin incubation concentration was maintained constant at 5 ug/ml. * P<0.05; ** P>0.05.
Figure 24:
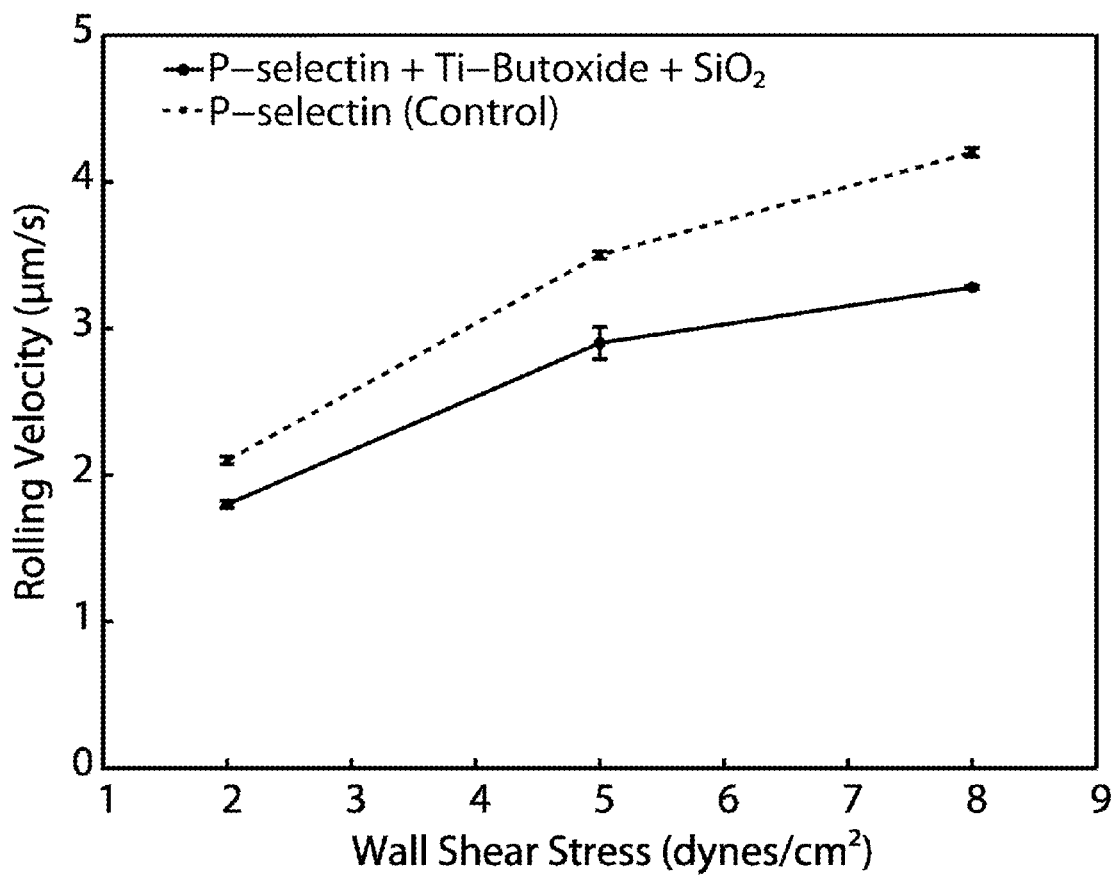
FIG. 24. Rolling studies on NP-coated and control tubes indicated a significantly slow rolling velocity of KG1a cells in NP-coated tubes. A statistically significant difference in rolling velocity was found at each shear stress studied.

The adhesion of cells to NP surfaces were also tested as a function of shear stress, and compared to smooth selectin-coated surfaces (FIG. 23). Cells rolling on the NP treated surface were found to have stronger adhesion, and rolling velocity appears to be a weaker function of shear stress on the NP surfaces (FIG. 24). At the lowest shear stress studied (0.5 dynes/cm$^2$), surface features were found to be statistically insignificant in altering cell behavior.

Unlike PLL, the titanium (IV) butoxide adhesive is not water-friendly. We observed that when it comes in contact with moisture, the adhesive layer spontaneously undergoes cross-linking reaction and crystallizes. As a result, cracking of the coating was observed mostly due to its exposure to humidity or the flowing aqueous sample prior to the adhesive curing. Since titanium (IV) butoxide is not comprised of amino acids, the coating has a wide range of pH in which it can maintain its integrity.

In this example, we significantly enhanced the capture of flowing cells in microtubes by coating NPs onto the cell contact surface; thereby increasing the surface roughness as well as gaining increased surface area. Using either titanium (IV) butoxide (inorganic) or PLL (organic) layers as adhesives, we immobilized the NPs to create novel nanosurfaces that resulted in enhanced protein absorption. Using both adhesives, the cell rolling velocities and the number of cells captured showed promising enhancement in NP-coated tubes. Negative controls (no P-selectin incubations, blocked with 5% BSA) PLL, and PLL with NP-coated surfaces confirmed that the enhancement is only observed when P-selectin is present. Furthermore, the immunofluorescence quantification indicated significantly higher presence of P-selectin compared to the control tube. Taken together, these results suggest that adhesive-immobilized NP coatings can significantly improve applications to isolate or sort cells using adhesive molecules under flow.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

The invention claimed is:

1. A method for trafficking cells comprising the steps of:
   a) providing a surface having nanoparticles immobilized thereon, said nanoparticles having selectin molecules attached thereon; and
   b) flowing the cells on the surface, wherein cells exhibiting selectin ligand molecules on the cell surface roll at a different velocity than cells that do not exhibit selectin ligand molecules on the cell surface allowing separation of the selectin ligand exhibiting cells from the cells that do not exhibit selectin ligand.

2. The method of claim 1, wherein step b) comprises subjecting the cells to a shear stress of 0.5 to 10 dynes/cm$^2$.

3. The method of claim 1, wherein the selectin molecule is P-selectin, E-selectin or L-selectin.

4. The method of claim 1, wherein the cells are CD34+ hematopoetic stem cells.

5. The method of claim 1, wherein the nanoparticles are immobilized to the surface via poly-L-lysine.

6. The method of claim 1, wherein the nanoparticles are immobilized to the surface via titanium butoxide.

7. A hollow device allowing the flow of cells therethrough comprising an inner surface having colloidal silica nanoparticles immobilized thereon, said nanoparticles having selectin or selectin-ligand molecules attached thereon, thereby allowing rolling of cells having selectin ligands thereon.

8. The device of claim 7, wherein the nanoparticles are immobilized on the inner surface via poly-L-lysine.

9. The device of claim 7, wherein the nanoparticles are immobilized on the inner surface via titanium butoxide.

* * * * *